United States Patent [19]

Nagata et al.

[11] 4,232,151
[45] Nov. 4, 1980

[54] DIHYDROTRIAZINYLTHIOOXACEPH-ALOSPORINS

[75] Inventors: Wataru Nagata, Nishinomiya; Yoshio Hamashima, Kyoto; Teruji Tsuji, Takasuki, all of Japan; William H. W. Lunn, Indianapolis, Ind.

[73] Assignee: Shionogi & Co., Ltd., Osaka, Japan

[21] Appl. No.: 924,375

[22] Filed: Jul. 13, 1978

[30] Foreign Application Priority Data

Jul. 14, 1977 [JP] Japan .................................. 52-84715

[51] Int. Cl.³ ............................................ C07D 498/00
[52] U.S. Cl. ..................................... 544/90; 544/182; 424/248.51; 542/424
[58] Field of Search ........................... 544/90; 542/424

[56] References Cited

U.S. PATENT DOCUMENTS

| | | | |
|---|---|---|---|
| 4,091,211 | 5/1978 | Montavon et al. | 544/21 |
| 4,138,486 | 2/1979 | Narisada et al. | 424/248.52 |

OTHER PUBLICATIONS

Kim et al., Tetrahedron Letters, No. 5, pp. 409–412 (1978).
Lednicer et al., The Organic Chemistry of Drug Synthesis, Frontispage, pp. 416–422, John Wiley and Sons, NY (1977).
Cama et al., J. Am. Chem. Soc., vol. 96, pp. 7582–7584 (1974).
Firestone et al., J. of Med. Chem., vol. 20, pp. 551 to 556 (1977).

*Primary Examiner*—John D. Randolph
*Attorney, Agent, or Firm*—Wenderoth, Lind & Ponack

[57] ABSTRACT

Dihydrotriazinylthiomethyl-oxacephem compounds represented by the formula:

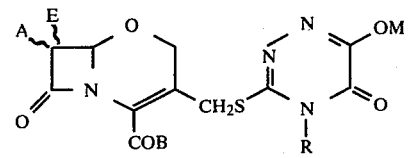

wherein A is amino or substituted amino; COB is carboxy, protected-carboxy or a carboxy salt; E is hydrogen or methoxy; M is hydrogen or hydroxy-protecting group; and R is lower alkyl are useful as antibacterial agents.

56 Claims, No Drawings

DIHYDROTRIAZINYLTHIOOXACEPHALOSPORINS

DETAILED DESCRIPTION OF THE INVENTION

This invention relates to potent antimicrobial agents, dihydrotriazinyl compounds represented by the formula (I):

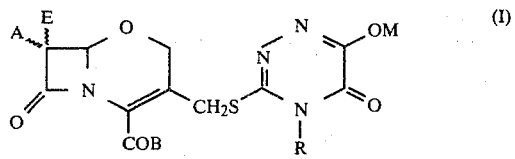

wherein A is amino or substituted amino; COB is carboxy, protected-carboxy or a carboxy salt; E is hydrogen or methoxy; M is hydrogen or hydroxy-protecting group; and R is lower alkyl.

1-Dethia-1-oxacephalosporin compounds are described in Japanese Unexamined Patent Publication No. 49-133546, Japanese Unexamined Patent Publication No. 51-149295 and the corresponding chemical literature, but compounds involving hydro-aromatic ring, 1-alkyl-5-hydroxy-6-oxo-1,6-dihydro-1,3,4-triazine moiety at the 3-position of 1-dethia-1-oxacephem structure have not yet been known. The inventors prepared dihydrotriazine compounds, investigated their antibacterial activity, and found that these exhibited remarkable properties in antimicrobial action, absorption, excretion and the like. This invention was completed based on this finding.

[I] Structure of dihydrotriazine compounds

Dihydrotriazine compounds (I) in this invention are derivatives of 1-dethia-1-oxa-3-(1-alkyl-5-hydroxy-6-oxo-1,6-dihydro-1,3,4-triazin-2-yl)thiomethyl-3-cephem-4-carboxylic acids represented by the formula (I) and have amino or substituted amino, and hydrogen or methoxy at the 7 position. The carboxy group at the 4 position may be protected.

The explanation of each group in a structure of dihydrotriazine compounds are as follows:

[1] Amino or substituted amino represented by A

Substituted amino means those at the side chain of natural or synthetic penicillins and cephalosporins and include organic or inorganic acyl amino, diacylamino, hydrocarbylamino, sulfenylamino, silylamino and acid addition salts with the amino group.

Representative of acyl groups involved in the substituted amino described above are acyl of carbonic acid (e.g. alkoxycarbonyl, aralkoxycarbonyl, aryloxycarbonyl), acyl of sulfuric acid, acyl of phosphoric acid (e.g. dialkoxyphosphinyl, dialkoxythiophosphonyl, alkoxyaminophosphoroyl), and the other inorganic acyl; alkanoyl, cycloalkanoyl, aralkanoyl, aroyl, alkylsulfonyl, arylsulfonyl, aralkylsulfonyl and the other organic acyl. These groups, if possible, may have a hetero atom or atoms in the main chain, unsaturation, or substituents as halogen (e.g. fluorine, chlorine, bromine), nitrogen group (e.g. amino, hydrazino, azido, alkylamino, arylamino, acylamino, alkylideneamino, acylimino, nitro), oxygen group (e.g. hydroxy, alkoxy, aralkoxy, aryloxy, acyloxy, oxo), sulfur group (e.g. mercapto, alkylthio, aralkylthio, arylthio, acylthio, thioxo, sulfo, alkylsulfonyl, sulfinyl, alkoxysulfonyl, aryloxysulfinyl), carbon group (e.g. alkyl, alkenyl, aralkyl, aryl, carboxy, carboalkoxy, carbamoyl, alkanoyl, aroyl, aminoalkyl, araalkanoyl, cyano) and phosphorus group (e.g. phospho, phosphoroyl). Acyl groups may also be diacyl groups derived from polybasic acids (e.g. phthaloyl, pyridine-2,3-dicarbonyl, maleoyl, succinoyl).

Representative acyls of the acylamino groups are:
(a) $C_1$–$C_{10}$ alkanoyl (e.g. formyl, acetyl, propionyl, butyryl, isobutyryl, valeryl, isovaleryl, pivaloyl, cyclohexylacetyl, octanoyl, decanoyl) or benzoyl;
(b) halo-$C_1$–$C_4$alkanoyl (e.g. chloroacetyl, trifluoroacetyl, chloropropionyl, bromopropionyl, chlorobutyryl);
(c) trifluoromethylthioacetyl or cyanoacetyl;
(d) (2- or 4-pyridon-1-yl)acetyl or (2-iminothiazolin-4-yl)acetyl;
(e) acyl groups represented by the formula:

wherein Q and Q' are hydrogen or methyl; Ar is a cyclic group such as phenyl, dihydrophenyl, furyl, thienyl, pyrrolyl, oxazolyl, isoxazolyl, oxadiazolyl, oxatriazolyl, thiazolyl, isothiazolyl, thiadiazolyl, thiatriazolyl, pyrazolyl, imidazolyl, triazolyl, tetrazolyl, pyridyl, pyrimidyl, pyrazinyl, pyridazinyl or triazinyl which cyclic groups can be substituted by halogen, lower alkyl (e.g. methyl, ethyl, propyl, isopropyl, butyl, isobutyl, t-butyl, pentyl, hexyl), hydroxy, both halogen and hydroxy, lower alkoxy (e.g. methoxy, ethoxy, propoxy, t-butoxy, methylenedioxy, ethylenedioxy), acyloxy (e.g. formyloxy, acetyloxy, propionyloxy, pentanoyloxy, carbamoyloxy, benzoyloxy, methoxycarbonyloxy, ethoxycarbonyloxy, t-butoxycarbonyloxy, benzyloxycarbonyloxy, nitrobenzyloxycarbonyloxy, methoxybenzyloxycarbonyloxy), aralkyloxy (e.g. benzyloxy, methoxybenzyloxy, aminobenzyloxy, methylbenzyloxy, isopropylbenzyloxy, nitrobenzyloxy, diphenylmethoxy, phthalidyloxy), aryloxy (e.g. phenoxy, tolyloxy, xylyloxy, indanyloxy), amino, acylamino (e.g. $C_1$–$C_{10}$alkanoylamino, lower-alkanesulfonylamino), hydroxymethyl, aminomethyl or the like;

(f) acyl groups represented by the formula:

wherein Ar, Q and Q' are the same as mentioned above and G is oxygen or sulfur;

(g) acyl groups represented by the formula:

wherein Ar is the same as mentioned above; T is (i) hydroxy or acyloxy as described above; (ii) carboxy, carboxy protected by lower alkoxy, aralkoxy or aryloxy as described above, cyano, or carbamoyl; (iii) sulfo or lower alkoxysulfonyl;

(h) acyl groups represented by the formula:

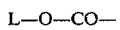

wherein L is t-butyl, 1,1-dimethylpropyl, cyclopropylmethyl, 1-methylcyclohexyl, isobornyl, ethoxy-t-butyl, 2-alkanesulfonylethyl, 2,2,2-trichloroethyl, benzyl, methoxybenzyl, nitrobenzyl, aminobenzyl, diphenylmethyl, tolylmethyl, phenyl, xylyl or pyridylmethyl;

(i) acyl groups represented by the formula:

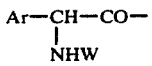

wherein Ar is the same as mentioned above; W is hydrogen, $C_1$-$C_{10}$ alkanoyl or halo-$C_1$-$C_4$ alkanoyl, or a group represented by the formula: Ar—CQQ'—CO— (as mentioned above), Ar—CO—, LOCO—,

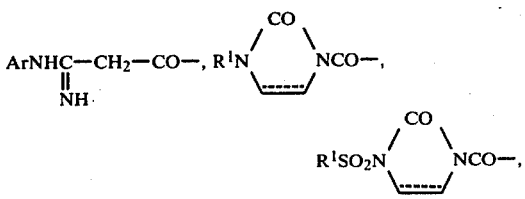

$R^1$NHCON$R^2$—CO—, $R^1$NHCSN$R^2$CO—,

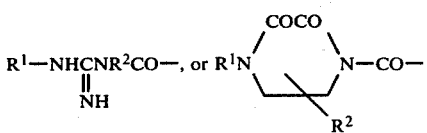

wherein Ar and L are as defined above, and $R^1$ and $R^2$ are hydrogen, $C_1$-$C_4$ alkyl (e.g. methyl, ethyl, propyl, t-butyl) or $C_1$-$C_{10}$ alkanoyl; or W is an enolic group of active carbonyl compounds represented by the formula

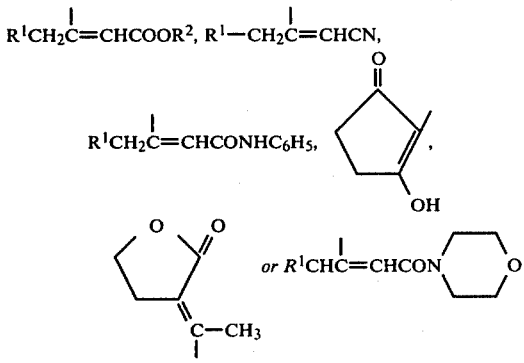

wherein $R^1$ and $R^2$ are the same as mentioned above; or NHW is diacylamido such as phthalimido or succinimido;

(j) acyl groups represented by the formula:

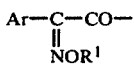

wherein Ar and $R^1$ are the same as mentioned above;
(k) 5-aminoadipoyl in which the carboxy or amino group is optionally protected with a conventional carboxy or amino protecting group. Substituted amino may be diacylamino derived from $C_4$ to $C_{10}$ polybasic acids.

Representative substituents in the hydrocarbonated amino are hydrocarbyl such as 1-carbethoxy-1-propen-2-yl, 1-carbamoyl-1-propen-2-yl, 1-N-phenylcarbamoyl-1-buten-2-yl, 1-propen-2-yl, 1-phenylpentene-2-yl, methyl, t-butyl and trityl, and univalent or bivalent hydrocarbon group such as methylidene, ethylidene, 1-halo-2-phenylethylidene, 1-methoxybenzylidene, 1-chlorobenzylidene, 1-loweralkoxy-2-phenylethylidene, 1-loweralkoxy-2-phenoxyethylidene and di-t-butyl-4-hydroxybenzylidene.

Organic silyl (e.g. trimethylsilyl, methoxydimethylsilyl, dimethoxymethylsilyl) and organic stannyl (e.g. trimethylstannyl) are also conventional amino protecting groups.

Substituted amino A includes a group convertible into amino or amido such as azido, isocyanato and isocyano.

The group A containing highly reactive part may be protected for purpose of preparation or preservation. When Compounds (I) are intermediates, the structure of them are widely variable, because the group A can be converted into the amino group and then the amino replaced with the desirable A group. Particularly, groups represented by the formula:

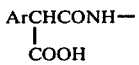

or the esters thereof and groups represented by the formula:

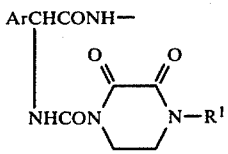

are important.

[2] Carboxy or protected carboxy COB

Carboxy protecting groups include ones ordinarily used in the field of penicillin and cephalosporin chemistry for temporary protection of carboxy group. Representative of them are esters such as alkyl esters (e.g. methyl-, ethyl-, trichloro-ethyl-ester), haloalkyl esters (e.g. chloroethyl-, 2-bromoethyl-, 2-iodoethyl-, 2-bromopropyl- ester), acylalkyl ester (e.g. phenacyl-, 4-chlorophenacyl- ester), alkoxyalkyl esters (e.g. methoxymethyl, 1-methoxyethyl-, ethoxymethyl- ester), acyloxyalkyl esters (e.g. acetoxymethyl, 1-acetoxyethyl, pivaloyloxymethyl-, 1-pivaloyloxyethyl-, ethoxycarbonyloxymethyl- and phthalidyl- ester), aralkyl esters (e.g. benzyl-, methoxybenzyl-, indanyl, nitrobenzyl-, diphenylmethyl-, trityl- ester), aryl esters (e.g. phenyl-, naphthyl- ester), metalic esters (e.g. trimethylsilyl, trimethyltin- ester) and like esters, acid anhydrides, thiol esters, amides, hydrazides, azides and the like carboxy derivatives. These carboxy derivatives, when possible, may involve above-mentioned halogen atoms, sulfur-, oxygen-, nitrogen-, carbon- group, and other substituents or may involve unsaturated bond.

Among these carboxy derivatives, ones having groups which are stable in reaction medium and which can be removed without any undesired change in other parts of the molecule after termination of the reaction, are important. Representatives of them are haloalkyl-, acylalkyl-, alkoxyalkyl-, acyloxyalkyl-, aralkyl-esters, and dialkylhydrazides. The group COB can also be a carboxy salt (e.g. sodium-, potassium-, magnesium-, aluminum-, alkylamine-salts). Pharmaceutically acceptable salts such as alkali metal salts and lower alkylamine salts are preferred.

[3] Hydrogen or methoxy group E

Regardless of structure E being hydrogen or methoxy, Compounds (I) exhibit potent antibacterial activity, but ones in which E is methoxy, are more stable against lactamase and exhibit a broad spectrum antibacterial activity.

[4] Alkyl groups R

R represents lower alkyls such as methyl, ethyl, propyl, isopropyl, butyl, isobutyl, pentyl, cyclohexyl, cyclopropylethyl, octyl and the like, preferably methyl.

[5] Hydroxy-protecting groups M

Hydroxy-protecting groups M are introduced for convenience of preparation or absorption and converted into hydrogen afterwards. The group M includes hydroxy-protecting groups ordinarily used in the field of penicillin or cephalosporin chemistry for protecting a hydroxy, for example, acyls (e.g. formyl, haloacetyl, oxalyl, the above-mentioned groups represented by the formula: L—OCO—), ethers (e.g. methoxymethyl-, ethoxymethyl-, tetrahydrofuranyl-, tetrahydropyranyl-, t-butyl-, 2-hydroxy-t-butyl- ethers), and silyl groups (e.g. trimethylsilyl, methoxydimethylsilyl, ethylenedioxymethylsilyl).

Dihydrotriazines compounds (I) of this invention include the following compounds and the pharmaceutically acceptable salts thereof listed in Table.

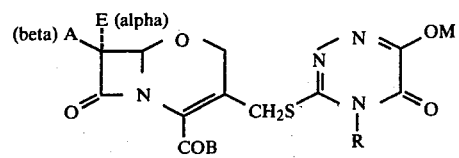

provided that the compounds of Nos. 13, 14 and 15 possess the following configuration:

| | A | E | M | R | COB |
|---|---|---|---|---|---|
| 1 | $H_2N-$ | H— | —H | $CH_3-$ | $-COOCHPh_2$ |
| 2 | " | " | $-COOC_4H_9\text{-}t$ | " | $-COOCH_2\text{-}C_6H_4\text{-}NO_2$ |
| 3 | " | " | —H | $C_2H_5-$ | $-COOCH_2CCl_3$ |
| 4 | " | " | " | $C_3H_7-$ | $-COOCH_2Ph$ |
| 5 | $PhCH_2CONH-$ | " | $-COO\text{-}bornyl$ | $CH_3-$ | $-COOCHPh_2$ |
| 6 | " | " | " | " | $-COOCH_2\text{-}C_6H_4\text{-}NO_2$ |
| 7 | " | " | —H | " | " |
| 8 | " | " | " | " | $-COOH$ |
| 9 | thienyl-$CH_2CONH-$ | " | " | " | " |
| 10 | (2-amino-thiazol-4-yl)-$CH_2CONH-$ | " | " | " | " |
| 11 | " | " | " | " | $-COOCHPh_2$ |
| 12 | (isoxazol-3-yl)-$CH_2CONH-$ | " | " | " | $-COOH$ |
| 13 | $\alpha-PhCONH-$ | $\beta-H-$ | " | " | " |
| 14 | $\alpha-PhC(Cl)=N-$ | " | $-COO\text{-}bornyl$ | " | $-COOCH_2\text{-}C_6H_4\text{-}NO_2$ |
| 15 | $\alpha-PhC(OCH_3)=N-$ | " | " | " | " |
| 16 | HO-$C_6H_4$-CH($NH_2$)CONH— | H— | H— | " | $-COOH$ |
| 17 | HO-$C_6H_4$-CH(t-BuOCONH)CONH— | " | " | " | $-COOCHPh_2$ |
| 18 | " | " | $-COOC_4H_9\text{-}t$ | " | $-COOCH_2\text{-}C_6H_4\text{-}NO_2$ |
| 19 | PhCH(OH)CONH— | " | H— | " | $-COOH$ |

-continued

| | A | E | M | R | COB |
|---|---|---|---|---|---|
| 20 | PhCHCONH—<br>    |<br>    COOH | " | " | " | " |
| 21 | PhCHCONH—<br>    |<br>    COO-(indanyl) | " | " | " | " |
| 22 | HO—C₆H₄—CHCONH—<br>    |<br>    COOH | " | " | " | " |
| 23 | HO—C₆H₃(F)—CHCONH—<br>    |<br>    COOH | " | " | " | " |
| 24 | F,HO—C₆H₃—CHCONH—<br>    |<br>    COOH | " | " | " | " |
| 25 | HO—C₆H₄—CHCONH—<br>    |<br>    NHCONCH₃<br>    CH₃NHCO | " | " | " | " |
| 26 | PhCHCONH—<br>    |<br>    NH-CO-imidazolidinone(NH) | " | " | " | " |
| 27 | HO—C₆H₄—CHCONH—<br>    |<br>    NH-CO-imidazolidinone(N-SO₂CH₃) | " | " | " | " |
| 28 | HO—C₆H₄—CHCONH—<br>    |<br>    NH-CO-dioxopiperazine(N-C₂H₅) | " | " | " | " |
| 29 | " | " | " | | —COOCH₂—C₆H₄—NO₂ |
| 30 | H₂NCOO—C₆H₄—CHCONH—<br>    |<br>    NH-CO-dioxopiperazine(N-C₂H₅) | " | " | " | —COOH |
| 31 | 2-furyl—C(=NOCH₃)—CONH— | " | " | " | " |
| 32 | HCHO— | " | " | " | " |
| 33 | CF₃SCH₂CONH— | " | " | " | " |
| 34 | NCCH₂CONH— | " | " | " | " |
| 35 | PhOCH₂CONH— | " | " | " | " |
| 36 | PhCHCONH—<br>    |<br>    OCHO | " | " | " | " |

-continued

| | A | E | M | R | COB |
|---|---|---|---|---|---|
| 37 | PhCHCONH— / OH | " | " | " | " |
| 38 | PhCH₂OCONH— | " | " | " | " |
| 39 | (bicyclic)OCONH— | " | (bicyclic)—COO— | " | —COOCH₂Ph |
| 40 | Cl₃CCH₂OCONH— | " | " | " | " |
| 41 | H₂N— | CH₃O— | —H | " | —COOH |
| 42 | " | " | " | " | —COOCH₂Ph |
| 43 | " | " | " | " | —COOCHPh₂ |
| 44 | " | | | " | —COOCH₂—⟨⟩—NO₂ |
| 45 | " | " | —COOC₄H₉-t | " | " |
| 46 | " | " | " | " | —COOCH₂Ph |
| 47 | " | " | —H | C₂H₅— | —COOCH₂Ph |
| 48 | " | " | " | C₃H₇— | —COOCH₂Ph |
| 49 | HCONH— | " | " | CH₃— | —COOH |
| 50 | CF₃SCH₂CONH— | " | " | " | " |
| 51 | NCCH₂CONH— | " | " | " | " |
| 52 | O=⟨pyridone⟩NCH₂CONH— | | | | |
| 53 | (aminothiazolyl)CH₂CONH— | " | " | " | " |
| 54 | " | " | " | " | —COOCHPh₂ |
| 55 | BrCH₂COCH₂CONH— | " | " | " | " |
| 56 | PhCH₂CONH— | " | " | " | " |
| 57 | " | " | " | " | —COOH |
| 58 | (thienyl)CH₂CONH— | " | " | " | " |
| 59 | " | " | " | " | —COOCH₂Ph |
| 60 | (tetrazolyl)N—CH₂CONH— | " | " | " | " |
| 61 | " | " | " | " | —COOH |
| 62 | (isoxazolyl)CH₂CONH— | " | " | " | " |
| 63 | PhCH₂C(Cl)=N— | " | " | " | " |
| 64 | PhCH₂C(OCH₃)=N— | " | " | " | —COOCH₂Ph |
| 65 | " | " | " | " | —COOCHPh₂ |
| 66 | PhOCH₂CONH— | " | " | " | —COOCH₂Ph |
| 67 | " | " | —COOC₄H₉—t | " | —COOCHPh₂ |
| 68 | " | | | | —COOCH₂—⟨⟩—NO₂ |
| 69 | PhCHCONH— / OCHO | " | —H | " | —COOCH₂Ph |
| 70 | PhCHCONH— / OH | CH₃—O— | " | " | —COOH |
| 71 | PhCHCONH— / COOH | " | " | " | " |
| 72 | HO—⟨⟩—CHCONH— / COOH | " | " | " | " |

-continued

| | A | E | M | R | COB |
|---|---|---|---|---|---|
| 73 | 3-HO-C6H4-CH(COOH)-CONH- | " | " | " | " |
| 74 | 4-HO-2-F-C6H3-CH(COOCHPh2)-CONH- | " | " | " | " |
| 75 | 5-HO-2-F-C6H3-CH(COOH)-CONH- | " | " | " | " |
| 76 | 4-H2NCOO-C6H4-CH(COOH)-CONH- | " | " | " | " |
| 77 | 4-H2NCOO-C6H4-CH(COOCHPh2)-CONH- | " | " | " | —COOCHPh2 |
| 78 | 4-CH3O-C6H4-CH2O-C6H4-CH(COO-CH2-C6H4-OCH3)-CONH- | " | " | " | " |
| 79 | 2-thienyl-CH(COOCHPh2)-CONH- | " | " | " | " |
| 80 | 2-thienyl-CH(COOH)-CONH- | " | " | " | —COOH |
| 81 | PhCH(NH2)CONH- | CH3O— | " | " | " |
| 82 | 4-HO-C6H4-CH(NH2)-CONH- | " | " | " | " |
| 83 | 4-H2NCOO-C6H4-CH(NH2)-CO- | " | " | " | " |
| 84 | PhCH(NH-C(CH3)=CHCOOCH3)-CONH- | " | " | " | —COOCHPh2 |
| 85 | 4-HO-C6H4-CH(NHCOOC4H9-t)-CONH- | " | " | " | " |
| 86 | 4-H2NCOO-C6H4-CH(NHCOOC4H9-t)-CONH- | " | " | " | " |
| 87 | 4-HO-C6H4-CH(NH-C(=O)-N(CH3)-CONHCH3)-CONH- | " | " | " | " |

| A | E | M | R | COB |
|---|---|---|---|---|
| 88 HO—⟨C₆H₄⟩—CH(NH-)CONH— where NH is connected to O=CN ring with NC₂H₅, two C=O (piperazine-2,3-dione with N-ethyl) | " | " | " | " |
| 89 H₂NCOO—⟨C₆H₄⟩—CH(NH-)CONH— where NH connected to O=CN ring with NC₂H₅, dione | " | " | " | " |
| 90 HO—⟨C₆H₄⟩—CH(NH-)CONH— where NH—C(=O) and O=CN—NSO₃CH₃ (ring) | " | " | " | " |
| 91 HO—⟨C₆H₄⟩—CH(NH-)CONH— where NH—C(=O) and O=CN—NH (ring) | " | " | " | " |
| 92 ⟨furan⟩-2-C(=NOCH₃)—CONH— | " | " | " | " |
| 93 PhCH₂OCONH— | " | " | " | —COOCH₂Ph |
| 94 ⟨bornyl⟩—OCONH— | " | " | " | —COOCHPh₂ |
| 95 Cl₃CCH₂OCONH— | " | " | " | " |

[II] Use, Dosage and Antibacterial Activity

Compounds (I) exhibit potent antibacterial activity and are useful as antibacterial agent for human, animals or plants. Compounds (I) may be administered to human or warm-blood animals, for example at a daily dose of 0.1–10 mg per 1 kg of body weight orally or parenterally in a conventional manner. Particularly, pharmaceutically acceptable carboxy salt of Compounds (I) may be administered in a form of solution by means of intravenous injection, intramuscular injection or subcutaneous injection. Compounds (I) may be put in ampoules in a form of solution, or preferably those are enclosed in ampoules in forms of crystals, powder, microcrystals, lyophilizate or the like and administered as a solution immediately before use.

Compounds (I), wherein A is arylglycylamino or pharmaceutically acceptable esters of aryl-malonylamino, such as indanyl-, alkanoyloxymethyl-, alkoxycarbonyloxymethyl-, phenacyl-, substituted phenacyl-, phthalidyl- and aryl-esters can orally be absorbed, so those may be administered orally to human or animals in forms of powder, tablets, granules, capsules, troches, dry syrups, suspensions, solutions, emulsions, inhalants or the like. Further, those may be administered as suppositories, eye lotion, powder for topical use, ointments or the like. Unit dosage forms such as tablets, capsules, ampoules, vials and the like are most preferable. These formulations also provide a method for treating infections caused by bacteria sensitive to the compounds of this invention. Compounds (I) of this invention are ordinarily administered at a dose of 1–40 mg/kg a day for injection or 10–400 mg/kg a day for oral administration, or 1 μg–1 mg a day for topical application, the dosage, however, can be increased or decreased in accordance with sensitivity of bacteria, times of administration, condition of patient and the like.

Dihydrotriazine Compounds (I) are up to about 32 times as strong as the corresponding dihydrotriazinyl cephalosporins in vitro antibacterial activity, so those are potent antibacterial agent against gram positive and negative bacteria. The protective effect against infections caused by *Escherichia coli* in vivo are generally 1–4 times as effective as the corresponding 1-methyl-tetrazol-5-ylthio-1-dethia-1-oxacephalosporins. Compounds (I) are further effective against bacteria practically resistant to commercially available cephalosporins, for example, Enterobacter, Serratia, indole-positive Proteus, and the like at the same level of MIC against sensitive bacteria (e.g. MIC less than 10 γ/cc).

[III] Preparation

Dihydrotriazine Compounds (I) may be prepared, for example, in the following manner.

(1) Cyclization

2-Oxoazetidine Compounds (II) may be cyclized by heating to yield Dihydrotriazine Compounds (I) as shown in the following reaction scheme.

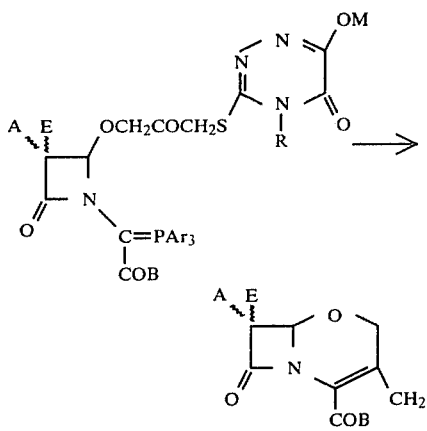

This reaction may be carried out by heating at about 70° to 150° C. for several hours in an inert solvent such as toluene, xylene, methylene chloride, dioxane, tetrahydrofuran and the like.

The compounds having phosphonyl group in place of arylphosphoranylidene group may also be cyclized on treatment with bases to yield the objective ones, and the 2-oxo-4-hydroxy-1-[α-carboxy-β-(1-methyl-5-hydroxy-6-oxo-1,6-dihydro-1,3,4-triazin-2-yl)thiomethyl-γ-halopropyl]azetidine derivatives may be cyclized on dehydrohalogenation reaction to yield the object ones.

(2) Substitution Reaction at Amino group

Compounds (I) wherein A is acylamino may be prepared from the compounds wherein A is amino on treatment with the reactive derivatives having the desirable acyl groups (e.g. halogenides, anhydrides, reactive esters, reactive amides, azides) in a conventional manner. The following examples are provided to illustrate the acylations according to the classification of the species of the reactive derivatives.

(i) Free acids

Compounds (I) wherein A is amino are reacted with 1 to 2 molar equivalent of free acids in the presence of 1 to 2 molar equivalent of condensing agent such as carbodiimides (e.g. N,N'-diethylcarbodiimide, N,N'-dicyclohexylcarbodiimide), carbonyl compounds (e.g. carbonylimidazoles), isoxazolinium salts, acylamino compounds (e.g. 2-ethoxy-1-ethoxycarbonyl-1,2-dihydroquinoline) and the like, preferably in a solvent not having active hydrogen such as halogenated hydrocarbons, nitriles, ethers, amides, their mixture or the like.

(ii) Acid anhydrides

Acid anhydrides include symmetric anhydrides, mixed anhydrides [e.g. mixed anhydrides of mineral acids and particularly alkyl- or aralkyl-hemicarbonate; mixed anhydrides of mineral acids and alkanoic acids or sulfonic acids], intramolecular anhydrides (e.g. ketones, isocyanates) and the like acid anhydrides.

Compounds (I) wherein A is amino are reacted with 1 to 2 molar equivalents of acid anhydrides in the presence of 1 to 10 molar equivalents of acid acceptor such as inorganic bases (e.g. oxide, hydroxide, carbonate, bicarbonate and the like of alkali metals and alkaline earth metals), organic bases (e.g. tetriary amines, aromatic bases), oxiranes (e.g. alkyleneoxides, aralkyleneoxides) or the like, preferably in a solvent not having active hydrogen such as halogenated hydrocarbons, nitriles, ethers, amides, their mixtures or the like.

(iii) Acid halogenides

Compounds (I) wherein A is amino are reacted with 1 to 2 molar equivalents of acid halogenides, preferably in the presence of 1 to 10 molar equivalents of aforementioned acid acceptor in a solvent such as halogenated hydrocarbons, nitriles, ethers, ketones, water, dialkylamides, their mixtures and the like.

(iv) Reactive esters

Reactive esters include enolic esters (e.g. vinyl esters, isopropenyl esters), aryl esters (e.g. halophenyl esters, nitrophenyl esters), heterocycle-aromatic esters (e.g. esters with 1-hydroxybenzotriazole), esters with oxime, esters, with diacylhydroxyamine and the like esters of which acyl part is a desirable acyl group.

(v) Reactive amides

Aromatic amides (e.g. amides with imidazole, triazole, 2-ethoxy-1,2-dihydroquinoline), diacylanilide and the like are included.

(vi) O-Acylformamide compounds

For example, O-enolic ester salts of N,N-dimethylformamide are included.

(vii) Other reactive derivatives

More than 1 mole of the compounds described in (iv)-(vi) may be reacted in an aforementioned solvent not having active hydrogen or their mixture.

Any reactions described above may be carried out at about −50° to 100° C., preferably at −20° to 50° C. A reaction solvent may optionally be selected from the group consisting of halogenated hydrocarbons (e.g. methylene chloride, chloroform, dichloroethane, trichloroethane, chlorobenzene), ethers (e.g. diethyl ether, tetrahydrofuran, tetrahydropyran, anisole), ketones (e.g. acetone, methyl ethyl ketone, methyl isobutyl ketone, cyclohexanone, acetophenone), esters (e.g. ethyl acetate, butyl acetate, methyl benzoate), nitrohydrocarbons, nitriles (e.g. acetonitrile, benzonitrile), amides (e.g. formamide, acetamide, dimethylformamide, dimethylacetamide, hexamethylphosphorotriamide), sulfoxides, acids (e.g. formic acid, acetic acid), bases (e.g. butylamine, triethylamine, pyridine, picoline, quinoline), water and the like.

If required, the reaction may be promoted by stirring under innert gas while removing moisture.

(Introduction of the other substituents of amino)

The desirable silyl group, sulfenyl group, or hydrocarbon group may be introduced on action of the corresponding silylating agent such as silyl halogenide (e.g. trimethylsilyl chloride, methoxydimethylsilyl chloride, methylenedioxysilyl chloride) and silazane (e.g. hexamethylsilazane, bistrimethylsilyl acetamide), sulfenylating agent such as halogenated sulfenyl (e.g. O-nitrophenylsulfenyl chloride) or hydrocarbonating agent such as aldehydes (e.g. salicylic aldehyde) and ketones (e.g. acetoacetate, acetoacetamide) in a conventional manner.

Compounds (I) wherein A is amide are reacted with an enolic halogenating agent such as phosphorus pentachloride and the like to yield the compounds wherein A is 1-haloalkylideneamino, and the latter treated with alcohol to yield the compounds wherein A is alkoxyalkylideneamino.

In the aforementioned reactions (1) and (2), the amino group A may preliminarily be protected or activated in forms of iminohalides, iminoethers, isocyanates, enamines and the like.

(3) Removal of substituent of amino

Compounds (I) wherein A is free amino may be prepared from ones wherein A is substituted amino on action of solvolyzing agent, hydrogenolyzing agent, reducing agent or the like in a conventional manner. For example, Compounds (I) wherein A is amino may be prepared: by reaction with hydrazine, phosphorus pentachloride and alcohols, carbonium ion forming agents or the like, when the substituent of amino is acyl; by reduction or on treatment with Lewis acids such as aluminum chloride, when the substituent is alkoxycarbonyl or haloalkoxycarbonyl; on treatment with acids, when the substituent is silyl; or on treatment with bases, when the substituent is sulfenyl.

(4) Introduction of carboxy protecting group

Compounds (I) having a free carboxylic acid may be converted into these having a protected carboxy group in conventional manner such as esterification by alcohols and condensing agents, diazo compounds, halogenated hydrocarbons, silyl or stannyl compounds; salt formation by bases; hydrazido formation by hydrazine; anhydride formation by acid halogenides and bases; and the like.

(5) Removal of carboxy protecting group

Carboxy protecting groups may be removed in manner usually used in the field of penicillin and cephalosporin chemistry. For example, the following methods may be employed:

(i) Highly active esters, amides or anhydrides are hydrolyzed on treatment with water containing acids, bases or buffers.

(ii) Haloethyl-, benzyl-, nitrobenzyl-, methylbenzyl-, dimethylbenzyl-, diarylmethyl-, triarylmethyl-esters are mildly reduced in conventional manner such as by tin, zinc, chromic salt or the like and acids, or sodium dithionite, or catalytically hydrogenated in the presence of platinum, palladium, nickel or the like to yield the corresponding free carboxylic acids.

(iii) Benzyl-, methoxybenzyl-, methylbenzyl-, dimethylbenzyl, t-alkyl-, trityl-, diarylmethyl-, cyclopropylmethyl-, cyclopropylethyl-, sulfonylethyl-esters are converted into the corresponding free carboxylic acids on solvolysis by mineral acids, Lewis acids, sulfonic acids, strongly acidic carboxylic acids or the like, and if required, in the presence of cation acceptor such as anisole, phenol, thiophenol and the like.

(iv) Phenacyl-, ethinyl-, p-hydroxy-3,5-di-t-butylbenzyl esters are converted into the corresponding free carboxylic acids on hydrolysis in the presence of bases.

(6) Introduction of the methoxy group

Compounds (I) wherein E is methoxy may be prepared from those wherein E is hydrogen, for example, in the following manner:

(i) Compounds (I) wherein E is hydrogen are reacted with N-halogenating agent (e.g. hypohalite such as t-butylhypochlorite), alkali metal methoxide (e.g. lithium methylate, sodium methylate, potassium methylate) and reducing agents in methanol;

(ii) Compounds (I) wherein E is hydrogen are reacted with t-butylhypochlorite and methanol-base in the presence of N-lithium introducing agent such as phenyl lithium in a solvent such as tetrahydrofuran, and if required, followed by reduction;

(iii) Compounds (I) wherein E is hydrogen are reacted with t-butylhypochlorite in the presence of sodium borate in methanol and by-product, N-chloro compounds, is reduced by zinc, phosphite or the like;

(iv) Compounds (I) wherein E is hydrogen and A is aralkylideneamino are reacted with oxidizing agent and methylmercaptan, and then mercuric acetate-methanol, (v) Compounds (I) wherein E is hydrogen and A is p-hydroxyaralkylideneamino are reacted with oxidizing agent and then methanol;

(vi) Compounds (I) wherein E is hydrogen and A is isonitrile are reacted with oxidizing agent and methanol; and (vii) Compounds (I) wherein E is hydrogen and A is α-haloalkanoylamino is reacted with bromine-DBU or phosphorus pentachloridepyridine to yield the corresponding iminohalide compounds, if required, the latter reacted with trialkylsilylhalide or tetraalkylammonium halite and then base to yield the corresponding conjugated imino compounds, and the latter treated with methanol.

(7) Introduction of 1-alkyl-5-hydroxy-6-oxo-1,6-dihydro-1,3,4-triazin-2-ylthio group 7β-Substituted-amino-1-dethia-1-oxa-3-cephem-4-carboxylic acid derivatives having methyl substituted by leaving group at the 3 position are reacted with heterothiol salts having the above hetero thio group to yield the objective compounds (I). Examples of the leaving groups are those replaceable with the desired hetero-thio groups, such as halogens, alkanoyloxy, haloalkanoyloxy, sulfonyloxy and the like.

This reaction is carried out in a conventional manner, for example, if required, on addition of reaction accelerator such as bases in a solvent.

(8) Removal of hydroxy protecting group

Hydroxy protecting groups M may be selected from the groups which are readily removable without any undesired influence on other parts of the molecule. For example, carbonate such as t-butoxycarbonyl, benzyloxycarbonyl, dimethylbenzyloxycarbonyl, isobornyloxycarbonyl, trichloroethoxycarbonyl, sulfonylethoxycarbonyl, and cyclopropylmethoxycarbonyl, tetrahydropyranyl, active ether such as 1-alkoxycyclopentyl and methoxymethyl, and the like may be removed with acids.

Hydroxy protecting group M is introduced for convenience of synthesis or use, and replaced by hydrogen afterwards.

(9) Transformation of acyl group

Substituted amino of dihydrotriazine compounds (I) may be modified for protection of unstable group in reaction media, recovered afterwards, or for enhancement of antibacterial activity, or the like.

This reaction includes, for examle, acylation of hydroxy or amino, transformation of protected carboxy, benzyloxycarbonylamino and t-butoxycarbonylamino into free carboxy or amino, formation of aminothiazole ring by reaction of ω-haloacetoacetyl group with thiourea, and the like, which may be carried out in a well-known method.

Each reaction mentioned above may be carried out according to known unit process, for example, in a solvent under cooling or heating, if required, with stirring under innert gas.

The products may be isolated by means of extraction, washing, drying, adsorption, evaporation or the like, and purified by reprecipitation, crystalization, chromatography or the like.

More than two of the suitably selected reactions may be carried out at the same time.

[IV] Preparation of starting materials

Dihydrotriazine Compounds (I) in this invention may also be prepared, for example, in the manner as shown in the following FIG. 1 and FIG. 2.

FIG. 1

(Japanese Unexamined Patent Publication No. 52-65292)

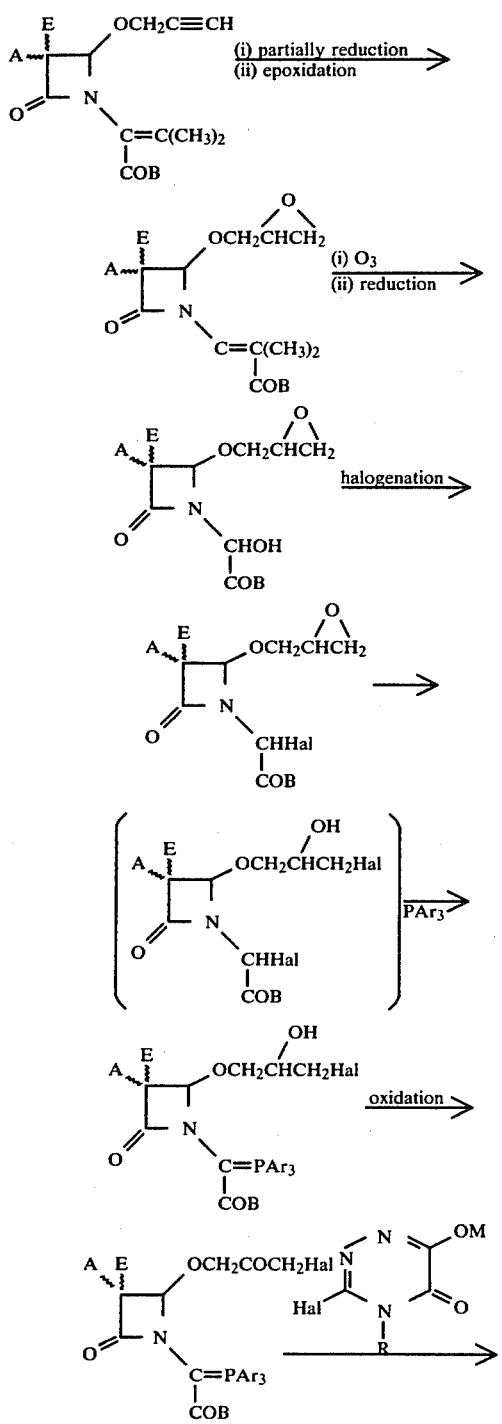

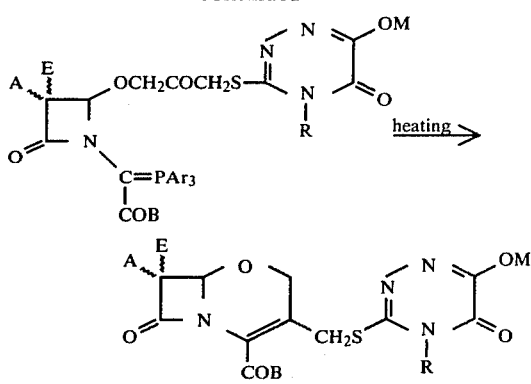

(wherein Hal is halogen; Ar is aryl, typically phenyl; A, COB, E, M, and R are the same as mentioned above)

FIG. 2

(Japanese Unexamined Patent Publication No. 52-65292)

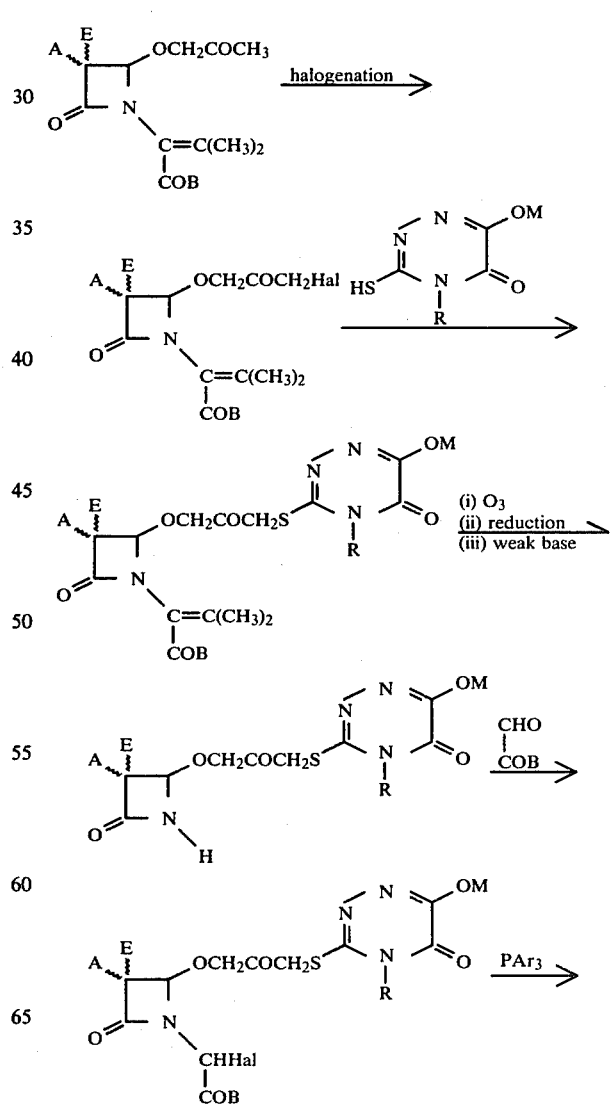

IR:ν$_{max}$$^{CHCl_3}$ 1783, 1710, 1690, 1590 cm$^{-1}$ (2) The following compounds are prepared in a procedure analogous to above (1).

| (R=CH₃) | A | E | M | COB |
|---|---|---|---|---|
| 1 | β—⟨phenyl⟩—CH₂CO— | α—H— | H— | —COOCHPh₂ |
| 2 | " | " | ⟨bornyl⟩—OCO— | —COOCH₂—⟨phenyl⟩—NO₂ |
| 3 | HO—⟨phenyl⟩—CHCO—<br>\|<br>COOCHPh₂ | " | H— | —COOCHPh₂ |
| 4 | " | α—CH₃O— | H— | —COOH |
| 5 | HO—⟨phenyl⟩—CHCO—<br>\|<br>NHCOOC₄H₉-t | " | " | —COOCHPh₂ |
| 6 | HO—⟨phenyl⟩—CHCO—<br>\|<br>NHCOOCH₂Ph | " | " | —COOCH₂Ph |

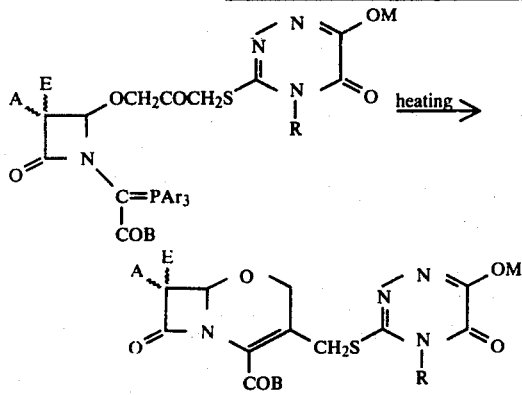

(Preferably M is hydroxy-protecting group such as t-butoxycarbonyl, isobornyloxy carboxy or the like in the reaction medium, and then converted into hydrogen afterwards.)
(wherein A, Ar, COB, E, Hal and M are the same as mentioned above)

These reactions are carried out according to the manner described in Japanese Unexamined Patent Publication No. 51-149295 and No. 52-65292. Representatives of them are concretely described in the following Preparations.

The following examples are provided to further illustrate this invention. Ph means phenyl group. Physical data for the compounds prepared hereinbelow are summarized in the tables following the reported examples and preparations.

EXAMPLE 1 (CYCLIZATION)

(1) A solution of 10.35 g of diphenylmethyl α-[3β-p-henylacetamide-3α-methoxy-4β-{3-(1-methyl-5-hydroxy-6-oxo-1,6-dihydro-1,3,4-triazin-2-yl)thio-2-oxopropyl}-oxy-2-azetidin-1-yl]-α-triphenylphosphoranyldeneacetate in 200 ml of dioxane is refluxed for 6 hours under heating and evaporated under reduced pressure. The residue is purified by chromatography on a column of 250 g of silica gel to yield 3.85 g of diphenylmethyl 7β-phenylacetamido-7α-methoxy-3-(1-methyl-5-hydroxy-6-oxo-1,6-dihydro-1,3,4-triazin-2-yl)thiomethyl-1-dethia-1-oxa-3-cephem-4-carboxylate in 52.7% yield.

EXAMPLE 2 (Amidation)

(1) To a solution of 1.8 mmoles of hemi-diphenylmethyl 2-fluoro-4-hydroxyphenylmalonate in 6 ml of methylene chloride are added 1.5 mmoles of triethylamine and 1.5 mmoles of oxalyl chloride under ice-cooling, and the mixture stirred for 1 hour, mixed with a solution of 0.4 mmole of diphenylmethyl 7β-amino-7α-methoxy-3-(1-methyl-5-hydroxy-6-oxo-1,6-dihydro-1,3,4-triazin-2-yl)thiomethyl-1-dethia-1-oxa-3-cephem-4-carboxylate in 4 ml of methylene chloride containing 0.15 ml of pyridine under ice-cooling. The reaction mixture is stirred for 2.5 hours, poured into 5% aqueous phosphoric acid solution and extracted with ethyl acetate. The extract is washed with water, dried and evaporated. The residue is chromatographed on 50 parts by volume of silica gel and eluted with a mixture of benzene and ethyl acetate (1:1) to yield 0.24 mmole of diphenylmethyl 7β-[α-(2-fluoro-4-hydroxyphenyl)-α-diphenylmethoxycarbonylacetamido]-7α-methoxy-3-(1-methyl-5-hydroxy-6-oxo-1,6-dihydro-1,3,4-triazin-2-yl)thiomethyl-1-dethia-1-oxa-3-cephem-4-carboxylate (60% yield).

NMR: δ$^{CDCl_3}$ (3.12s+3.15s)3H, 3.47s3H, 3.88brs2H, 4.23brs2H, 4.97brs1H, 5.00ss1H, 6.23–7.73m25H.

(2) When 0.8 ml of hemi-diphenylmethyl 3-thienylmalonate is employed in place of 1.8 mmoles of hemi-diphenylmethyl 2-fluoro-4-hydroxyphenylmalonate in the above Examples, 0.17 mmole of diphenylmethyl 7β-[α-(3-thienyl)-α-diphenylmethoxycarbonylacetamido]-7α-methoxy-3-(1-methyl-5-hydroxy-6-oxo-1,6-dihydro-1,3,4-triazin-2-yl)thiomethyl-1-dethia-1-oxa-3-cephem-4-carboxylate is produced.

IR: ν$_{max}$$^{CHCl_3}$ 1785, 1720, 1715, 1695, 1590 cm$^{-1}$ (3) To a solution of 4.57 mmoles of diphenylmethyl 7β-amino-3-(1-methyl-5-hydroxy-6-oxo-1,6-dihydro-1,3,4-triazin-2-yl)thiomethyl-1-dethia-1-oxa-3-cephem-4-carboxylte in 25 ml of acetonitrile is added 4.5 ml of bistrimethylsilylacetamide, and the mixture stirred at room temperature for 1 hour, and evaporated under reduced pressure. The residue is dissolved in tetrahydrofuran under ice-cooling, and mixed with a solution of active ester in tetrahydrofuran prepared from 4.57 mmoles of (4-hydroxyphenyl)-N-t-butoxycarbonylglycine, 4.57 mmoles of 1-hydroxy-1H-benzotriazole and 5.48 mmoles of N,N'-dicyclohexylcarbodiimide. The reaction mixture is stirred at 0° for 20 minutes and at room temperature for 60 minutes, poured into ice water-ethyl acetate and shaken. The organic layer is separated, washed with water, dried and evaporated under reduced pressure. The residue is chromatographed on 120 g of silica gel, and eluted with a mixture of chloroform and methanol (97:3). The eluate is concentrated to yield 3.16 mmoles of diphenylmethyl 7β-[N-t-butoxycarbonyl-α-(4-hydroxyphenyl)glycineamido]-3-(1-methyl-5-hydroxy-6-oxo-1,6-dihydro-1,3,4-triazin 2-yl)thiomethyl-1-dethia-1-oxa-3-cephem-4-carboxylate.

NMR: δ$^{CDCl_3}$ 1.43s9H, 3.37s3H, 5.03d(4 Hz)1H etc.

(4) To a solution of 0.154 mmoles of diphenylmethyl 7β-amino-7α-methoxy-3-(1-methyl-5-hydroxy-6-oxo-1,6-dihydro-1,3,4-triazin-2-yl)thiomethyl-1-dethia-1-oxa-3-cephem-4-carboxylate in 1 ml of methylene chloride are added 15.6 mg of triethylamine at −40° C. and then a solution of bromoacetoacetyl bromide (prepared from 0.013 ml of diketene) in methylene chloride, and the mixture allowed to stand at −40° to −30° C. for 60 minutes, mixed with 0.19 mmole of dimethylaniline and the same amount of bromoacetoacetyl bromide as mentioned above, and allowed to stand at −30° to −40° C. for 30 minutes. The reaction mixture is diluted with 10% aqueous phosphoric acid solution and poured into ethyl acetate-ice water. The organic layer is washed with water, dried, and evaporated under reduced pressure to yield 132 mg of diphenylmethyl 7β-bromoacetamido-7α-methoxy-3-(1-methyl-5-hydroxy-6-oxo-1,6-dihydro-1,3,4-triazin-2-yl)thiomethyl-1-dethia-1-oxa-3-cephem-4-carboxylate.

Rf=0.39 (silica gel TLC plate/ethyl acetate)

EXAMPLE 3 (Removal of the amino-protecting group)

(1) To a solution of 3.23 g of diphenylmethyl 7β-phenylacetamido-3-(1-methyl-5-hydroxy-6-oxo-1,6-dihydro-1,3,4-triazin-2-yl)thiomethyl-1-dethia-1-oxa-3-cephem-4-carboxylate in 30 ml of methylene chloride are added 2.55 ml of N,N-dimethylaniline and 1.51 ml of trimethylchlorosilane, and the mixture stirred at room temperature for 1 hour, mixed with 1.32 g of phosphorus pentachloride under cooling at −40° C., stirred for 1.5 hours, mixed with 12 ml of methanol at −60° C. and stirred at −60° C. for 5 minutes and then at 0° C. for 30 minutes. The reaction mixture is treated in a conventional manner to yield 2.38 g of diphenylmethyl 7-amino-3-(1-methyl-5-hydroxy-6-oxo-1,6-dihydro-1,3,4-triazin-2-yl)thiomethyl-1-dethia-1-oxa-3-cephem-4-carboxylate as colorless powder in 90.5% yield.

Rf=0.08 (silica gel plate/ethyl acetate)

(2) In a manner similar to that of above (1), diphenylmethyl 7β-phenylacetamido-7α-methoxy-3-(1-methyl-5-hydroxy-6-oxo-1,6-dihydro-1,3,4-triazin-2-yl)thiomethyl-1-dethia-1-oxa-3-cephem-4-carboxylate (1.34 g) is treated with N,N-dimethylaniline and dimethyl silyl dichloride in methylene chloride to yield a compound having a protected hydroxy on its triazine ring and the product is treated with methanol to yield 0.98 g of diphenylmethyl 7β-amino-7α-methoxy-3-(1-methyl-5-hydroxy-6-oxo-1,6-dihydro-1,3,4-triazin-2-yl)thiomethyl-1-dethia-1-oxa-3-cephem-4-carboxylate as powder in 89% yield.

Rf=0.21 (silica gel plate/ethyl acetate)

(3) Diphenylmethyl 7β-phenylacetamido-3-(1-methyl-5-isobornyloxycarbonyloxy-6-oxo-1,6-dihydro-1,3,4-triazin-2-yl)thiomethyl-1-dethia-1-oxa-3-cephem-4-carboxylate (129 mg) is treated with 37 mg of pyridine, 80 mg of phosphorus pentachloride and 1.5 ml of methanol in 5 ml of methylene chloride at −20° C. in a similar manner to that mentioned above (1) to yield 99 mg of toluene-p-sulfonate of the corresponding 7-free amino compound in 73.5% yield.

EXAMPLE 4 (Introduction of carboxy-protecting group)

(1) The compounds having a free carboxy given in each of the examples are dissolved in dilute aqueous sodium hydrogencarbonate solution to yield the corresponding sodium salts and the latter examined antibacterial activity; the results indicate that the salts exhibit strong antibacterial activity against gram positive and negative bacteria.

(2) 7β-[α-p-Hydroxyphenyl-N-(4-ethyl-2,3-dioxopiperazin-1-yl)carbonylglycyl]amino-7α-methoxy-3-(1-methyl-5-hydroxy-6-oxo-1,6-dihydro-1,3,4-triazin-2-yl)thiomethyl-1-dethia-1-oxa-3-cephem-4-carboxylic acid (118 mg) is dissolved in 3 ml of methanol and the insoluble materials are filtered off. The solution is diluted with 3 ml of ethanol and mixed with two equivalents of a solution of sodium 2-ethylhexanoate in isopropanol, and the precipitate collected by filtration and washed with ethanol, ethyl acetate and then ether to yield 49 mg of the corresponding sodium salts in 54% yield.

IR: $\nu_{max}^{KBr}$ 1775, 1710, 1685 cm$^{-1}$

EXAMPLE 5 (Removal of the carboxy-protecting group)

(1) To a solution of 148 mg of diphenylmethyl 7β-[α-(3-thienyl)-α-diphenylmethoxycarbonylacetamido]-7α-methoxy-3-(1-methyl-5-hydroxy-6-oxo-1,6-dihydro-1,3,4-triazin-2-yl)thiomethyl-1-dethia-1-oxa-3-cephem-4-carboxylate in 20 parts by volume of methylene chloride are added 4 parts by volume of anisole and 4 parts by volume of trifluoroacetic acid under ice-cooling, and the mixture stirred for 2 hours and evaporated under reduced pressure at room temperature. The residue is washed with ethyl ether to yield 77 mg of 7β-[α-(3-thienyl)-α-carboxyacetamido]-7α-methoxy-3-(1-methyl-5-hydroxy-6-oxo-1,6-dihydro-1,3,4-triazin-2-yl)thiomethyl-1-dethia-1-oxa-3-cephem-4-carboxylic acid as light yellow powder in 35% yield.

IR: $\nu_{max}^{KBr}$ 1783, 1710, 1586 cm$^{-1}$ (2) The following compounds may be prepared in a similar manner to that mentioned in (1) to (5).

| (R=CH$_3$) | A | E | M | COB | * |
|---|---|---|---|---|---|
| 1 | ⟨phenyl⟩—CH$_2$CO— | —H | H | COOH | |
| 2 | " | —OCH$_3$ | " | " | |
| 3 | H$_2$N—⟨thiazole-S⟩—CH$_2$CO— | —H | " | " | |

-continued

| (R=CH₃) | A | E | M | COB | * |
|---|---|---|---|---|---|
| 4 | " | —OCH₃ | " | " | |
| 5 | HO—C₆H₄—CH(NH₂)CO— | —H | " | " | N—BOC |
| 6 | " | —OCH₃ | " | " | " |
| 7 | HO—C₆H₄—CH(NHCON(—CH₂CH₂—)N(C₂H₅)C(O)C(O))CO— | —H | " | " | |
| 8 | " | —OCH₃ | " | " | |
| 9 | H₂NCOO—C₆H₄—CH(NHCON(—CH₂CH₂—)N(C₂H₅)C(O)C(O))CO— | —H | " | " | |
| 10 | " | —OCH₃ | " | " | |
| 11 | HO—C₆H₄—CH(NHCON(—CH₂CH₂—)NSO₂CH₃)CO— | —H | " | " | |
| 12 | " | —OCH₃ | " | " | |
| 13 | HO—C₆H₄—CH(NHCONCONHCH₃; CH₃)CO— | —H | H | COOH | |
| 14 | " | —OCH₃ | " | " | |
| 15 | H₂NCOO—C₆H₄—CH(NH₂·CF₃COOH)CO— | —OCH₃ | " | " | N—BOC |
| 16 | HO—C₆H₄—CH(COOH)CO— (meta-HO) | " | " | " | P—CH₃OC₇H₆ ester; O—CH₃OC₇H₆ ether |
| 17 | HO—C₆H₄—CH(COOH)CO— | " | " | " | O—CHPh₂ ester |
| 18 | H₂NCOO—C₆H₄—CH(COOH)CO— | " | " | " | O—CHPh₂ ester |
| 19 | HO—C₆H₃(F)—CH(COOH)CO— | " | " | " | O—CHPh₂ ester |

* Protecting group in the side chain of the starting material (3) A solution of 110 mg of p-nitrobenzyl 7β-phenylacetamido-3-(1-methyl-5-isobornyloxycarbonyloxy-6-oxo-1,6-dihydro-1,3,4-triazin-2-yl)thiomethyl-1-dethia-1-oxa-3-cephem-4-carboxylate in tetrahydrofuran-methanol (1:2) containing 0.03 ml of concentrated hydrochloric acid is shaken in the presence of 30 mg of 5% palladium-charcoal under hydrogen atmosphere for 4 7/12 hours, consuming 15.14 ml of hydrogen gas. The mixture is filtered and the filtrate evaporated under reduced pressure. The residue is chromatographed on 1.5 g of silica gel and eluted with chloroform-ethyl acetate (3:1) to yield 68 mg of 7-β-phenylacetamido-3-(1-methyl-5-isobornyloxycarbonyloxy-6-oxo-1,6-dihydro-1,3,4-triazin-2-yl)thiomethyl-1-dethia-1-oxa-3-cephem-4-carboxylic acid in 74.3% yield.

EXAMPLE 6 (Introduction of 7α-methoxy)

(1) To a solution of 385 mg of diphenylmethyl 7β-(α-p-hydroxyphenyl-N-t-butoxycarbonylglycyl)amino-3-(1-methyl-5-hydroxy-6-oxo-1,6-dihydro-1,3,4-triazin-2-yl)thiomethyl-1-dethia-1-oxa-3-cephem-4-carboxylate in 6 ml of dihydropyran is added 3 to 4 drops of phosphoric acid in 4 to 5 portions. After about 1 hour, the mixture is diluted with ethyl acetate, washed with 5% aqueous sodium hydrogencarbonate solution and then aqueous sodium chloride solution, dried and evaporated under reduced pressure. The residue is stirred with petroleum ether. The obtained residue (520 mg) is chromatographed on 10 g of silica gel and eluted with benzene-ethyl acetate (5:1) to yield 373 mg of diphenylmethyl 7β-(α-p-tetrahydropyranyloxyphenyl-N-t-butoxycarbonylglycyl)amino-3-(1-methyl-5-tetrahydropyranyloxy-6-oxo-1,6-dihydro-1,3,4-triazin-2-yl)thiomethyl-1-dethia-1-oxa-3-cephem-4-carboxylate.

(2) To a solution of 282 mg of the product of above (1) in a mixture of 6 ml of methylene chloride and 0.6 ml of methanol are added 50 μl of t-butylhypochlorite and 0.6 ml of a solution (2 mmoles/ml) of lithium methoxide in methanol, and the mixture stirred at −55° to −50° C. for 25 minutes, cooled to −78° C., mixed with 1 ml of dimethylsulfide and 0.5 ml of acetic acid, stirred for 15 minutes, and warmed to 0° C. The reaction mixture is mixed with ethyl acetate, washed with 5% aqueous sodium hydrogen-carbonate solution and aqueous sodium chloride solution and evaporated under reduced pressure. The residue (307 mg) is dissolved in 15 ml of methanol, mixed with 1.5 ml of 5% hydrochloric acid, allowed to stand at room temperature for 60 minutes, mixed with ethyl acetate, washed with 5% aqueous sodium hydrogen-carbonate solution and then aqueous sodium chloride solution, dried and evaporated. The residue (212 mg) is chromatographed on silica gel containing 10% water to yield 95 mg of diphenylmethyl 7β-(α-p-hydroxyphenyl-N-t-butoxycarbonylglycyl)amino-7α-methoxy-3-(1-methyl-5-hydroxy-6-oxo-1,6-dihydro-1,3,4-triazin-2-yl)thiomethyl-1-dethia-1-oxa-3-cephem-4-carboxylate as foamy material in 40% yield.

IR: $\nu_{max}^{CHCl_3}$ 1790, 1710, 1690, 1595, 1495 cm$^{-1}$.

EXAMPLE 7

To a solution of 2.903 g of p-nitrobenzyl 7α-phenylacetamido-3-chloromethyl-1-dethia-1-oxa-3-cephem-4-carboxylate in 20 ml of dimethylformamide is added a solution of sodium 1-methyl-5-hydroxy-6-oxo-1,6-dihydro-1,3,4-triazin-2-ylmercaptide (prepared from a suspension of 950 mg of the corresponding thiol in methanol by adding 30.9 ml of 0.193 M sodium methoxide and concentrating under reduced pressure) in dimethylformamide. After 30 minutes, the reaction mixture is diluted with methylene chloride, washed with 5% phosphoric acid and water, dried and evaporated under reduced pressure. The residue is chromatographed on silica gel and eluted with ethyl acetate-methylene chloride (1:1) to yield 1.80 g of p-nitrobenzyl 7β-phenylacetamido-3-(1-methyl-5-hydroxy-6-oxo-1,6-dihydro-1,3,4-triazin-2-yl)thiomethyl-1-dethia-1-oxa-3-cephem-4-carboxylate.

IR: $\nu_{max}^{KBr}$ 1790, 1710, 1690, 1670, 1650, 1585, 1520 cm$^{-1}$

NMR: $\delta^{CDCl_3+CD_3SOCD_3}$ 3.38s3H, 3.58s2H, 4.17s2H, 4.68s2H, 5.20d (4 Hz)1H, 5.47s2H, 5.63dd(4; 9 Hz)1H, 7.2–8.4m9H, 8.77d(9 Hz)1H, 12.6s1H.

The starting material may be prepared from 3.262 g of p-nitrobenzyl 7β-phenylacetamido-3-acetoxymethyl-1-dethia-1-oxa-3-cephem-4-carboxylate on reaction with 2.25 g of boron chloride in 60 ml of methylene chloride at room temperature for 60 minutes in more than 93% yield.

EXAMPLE 8 (Introduction of hydroxy-protecting group)

(1) To a solution of 52 mg of diphenylmethyl 7β-phenylacetamido-3-(1-methyl-5-hydroxy-6-oxo-1,6-dihydro-1,3,4-triazin-2-yl)thiomethyl-1-dethia-1-oxa-3-cephem-4-carboxylate in 1 ml of tetrahydrofuran is added 26 mg of isobornylchloroformate in the presence of 12 ml of N-methylmorpholine, and the mixture stirred for 40 minutes, diluted with ethyl acetate, washed with water, dried and evaporated under reduced pressure. The residue is chromatographed on 1.5 g of silica gel and eluted with benzene-ethyl acetate (3:1) to yield 36 mg of 5-isobornyloxycarbonyloxy-6-oxotriazinyl compound in 54.3% yield.

(2) The same starting material as (1) is treated with 2-equivalents of dimethyldichlorosilane and 4 equivalents of dimethylaniline to yield the corresponding silyl compound.

(3) p-Nitrobenzyl 7β-phenylacetamido-3-(1-methyl-5-hydroxy-6-oxo-1,6-dihydro-1,3,4-triazin-2-yl)thiomethyl-1-dethia-1-oxa-3-cephem-4-carboxylate (800 mg), N-methylmorpholine (200 mg) and 285 mg of isobornylchloroformate are dissolved in 25 ml of tetrahydrofuran and reacted at 0° C. for 2 hours. The reaction mixture is diluted with ethyl acetate, washed with water, dried and evaporated under reduced pressure. The residue is chromatographed on 35 g of silica gel and eluted with benzene-ethyl acetate (3:1) to yield 901 mg of the corresponding 5-isobornyloxycarbonyloxy-6-oxotriazinyl compound.

IR: $\nu_{max}^{CHCl_3}$ 3430, 1795, 1760, 1720, 1685, 1610, 1515, 1350 cm$^{-1}$ NMR: $\delta^{CDCl_3}$ 0.8–2.1 ml6H, 3.32s3H, 3.60s2H, 4.18s2H, 4.62s2H, 4.85t(6 Hz)1H, 5.00d(4 Hz)1H, 5.33ABq2H, 5.67dd(4; 9 Hz)1H, 6.50d(9 Hz) 1H, 7.2–8.2m9H.

(2) To a suspension of 62 mg of diphenylmethyl 7β-(α-p-hydroxyphenyl-N-t-butoxycarbonylglycyl)amino-3-(1-methyl-5-hydroxy-6-oxo-1,6-dihydro-1,3,4-triazin-2-yl)thiomethyl-1-dethia-1-oxa-3-cephem-4-carboxylate in 1 ml of dihydropyran is added 1 drop of phosphoric acid, and the mixture kept at room temperature for 50 minutes, diluted with ethyl acetate, washed with 5% aqueous sodium hydrogencarbonate and water, dried and evaporated. The residue is agitated in petroleum ether to yield 81 mg of diphenylmethyl 7β-(α-p-tetrahydropyranyloxyphenyl-N-t-butoxycarbonylglycyl)amino-3-(1-methyl-5-tetrahydropyranyloxy-6-oxo-1,6-dihydro-1,3,4-triazin-2-yl)thiomethyl-1-dethia-1-oxa-3-cephem-4-carboxylate.

EXAMPLE 9

A. Acylation of phenol (1) To a solution of 94 mg of diphenylmethyl 7β-(α-p-hydroxyphenyl-N-t-butoxycarbonylglycyl)amino-7α-methoxy-3-(1-methyl-5-hydroxy-6-oxo-1,6-dihydro-1,3,4-triazin-2-yl)thiomethyl-1-dethia-1-oxa-3-cephem-4-carboxylate in 2 ml of methylene chloride is added 0.5 ml of a solution of 6 μl of N-methylmorpholine and 16 μl of trichloroacetyl isocyanide in methylene chloride, and the mixture stirred for 30 minutes and pured into a mixture of ice water and ethyl acetate. The organic layer is separated, washed with water, dried and evaporated under reduced pressure. The residue is adsorbed on silica gel, and after 1 hour, slowly eluted with chloroform-methanol (98:2) mixture to yield 96 mg of diphenylmethyl 7β-(α-p-carbamoyloxyphenyl-N-t-butoxycarbonylglycyl)amino-7α-methoxy-3-(1-methyl-5-hydroxy-6-oxo-1,6-dihydro-1,3,4-triazin-2-yl)thiomethyl-1-dethia-1-oxa-3-cephem-4-carboxylate in 72% yield.

Rf=0.15 (TLC plate precoated by silica gel/-chloroform:methanol (9:1))

(2) The following compounds are preparable in a similar manner to that mentioned in (1).

| (R=CH$_3$) | A | E | M | COB |
|---|---|---|---|---|
| 1 | α- H$_2$NCOO—⟨phenyl⟩—CHCONH— ; β- C$_2$H$_5$N(piperazine-2,3-dione)NCONH | α—H | H | COOH or COOCHPh$_2$ |
| 2 | β—H$_2$NCOO—⟨phenyl⟩—CHCONH—, NH$_2$ | α—OCH$_3$ | " | COOH or COOCHPh$_2$ |
| 3 | β—H$_2$NCOO—⟨phenyl⟩—CHCONH—, COOH | " | " | COOH or COOCHPh$_2$ |
| 4 | β—H$_2$NCOO—⟨phenyl⟩—CHCONH—, COOCHPh$_2$ | " | " | COOH or COOCHPh$_2$ |

B. Acylation of amino group (1) To a suspension of 97 mg of 7β-(α-p-hydroxyphenylglycyl)amino-7α-methoxy-3-(1-methyl-5-hydroxy-6-oxo-1,6-dihydro-1,3,4-triazin-2-yl)thiomethyl-1-dethia-1-oxa-3-cephem-4-carboxylic acid trifluoroacetate in 2 ml of acetonitrile are added 0.5 ml of propylene oxide and 0.25 ml of O,N-bistrimethylsilyacetamide, and the mixture stirred at room temperature for 10 minutes and mixed with 45 mg of N-methylcarbamoyl chloride at 0° C. The mixture is stirred for 1 hour, mixed with methanol and evaporated under reduced pressure. The residue is triturated in ether to yield 7η-[α-p-hydroxyphenyl-N-(N$^1$,N$^3$-dimethylureido)carbonylglycyl]amino-7α-methoxy-3-(1-methyl-5-hydroxy-6-oxo-1,6-dihydro-1,3,4-triazin-4-yl)thiomethyl-1-dethia-1-oxa-3-cephem-4-carboxylic acid as powder in nearly quantitative yield.

Rf=0.19 (TLC plate precoated by silica gel/acetic acid:ethyl acetate:water (1:5:1))

(2) To a suspension of 69 mg of 7β-(α-p-carbamoyloxyphenylglycyl)amino-7α-methoxy-3-(1-methyl-5-hydroxy-6-oxo-1,6-dihydro-1,3,4-triazin-2-yl)thiomethyl-1-dethia-1-oxa-3-cephem-4-carboxylic acid trifluoroacetate in 2 ml of acetonitrile are added 0.4 ml of propylene oxide and 0.2 ml of O,N-bis-trimethylsilylacetamide, and the mixture stirred at room temperature for 15 minutes, cooled with ice, and mixed with 41 mg of 4-ethyl-2,3-dioxopiperazin-1-ylcarbonyl chloride. The mixture is stirred for 40 minutes and evaporated under reduced pressure. The residue is agitated in petroleum ether, ether and ethyl acetate successively to yield 62 mg of 7β-[α-p-carbamoyloxyphenyl-N-(4-ethyl-2,3-dioxopiperazin-1-yl)carbonylglycyl]amino-7α-methoxy-3-(1-methyl-5-hydroxy-6-oxo-1,6-dihydro-1,3,4-triazin-2-yl)thiomethyl-1-dethia-1-oxa-3-cephem-4-carboxylic acid as colorless powder in 83% yield.

Rf=0.33 (TLC plate precoated by silica gel/acetic acid: ethyl acetate:water (1:5:1)).

The following compounds are preparable in a similar manner to that described in (1) and (2) immediately hereinabove.

| (R=CH$_3$) | A | E | M | COB |
|---|---|---|---|---|
| 1 | HO—⟨phenyl⟩—CHCONH, HNCON(piperazine-2,3-dione)NC$_2$H$_5$ | H | H | COOH |
| 2 | " | " | " | COOCH$_2$—⟨phenyl⟩—NO$_2$ |
| 3 | " | CH$_3$O— | " | COOH |
| 4 | H$_2$NCOO—⟨phenyl⟩—CHCONH—, NHCON(piperazine-2,3-dione)NC$_2$H$_5$ | H— | " | " |
| 5 | HO—⟨phenyl⟩—CHCONH—, NHCONCONHCH$_3$, CH$_3$ | " | " | " |

-continued

| (R=CH₃) | A | E | M | COB |
|---|---|---|---|---|
| 6 | HO—⌬—CHCONH— <br> \|  <br> NHCOOC₄H₉-t |  |  | COOCHPh₂ |
| 7 | " | CH₃O— | " | " |
| 8 | H₂NCOO—⌬—CHCONH— <br> \| <br> NHCOOC₄H₉-t | " | " | " |

C. Cyclization of thiazole (1) To a solution of 132 mg of diphenylmethyl 7β-bromoacetoacetamido-7α-methoxy-3-(1-methyl-5-hydroxy-6-oxo-1,6-dihydro-1,3,4-triazin-2-yl)thiomethyl-1-dethia-1-oxa-3-cephem-4-carboxylate in a mixture of 1 ml of tetrahydrofuran and 1 ml of methanol is added a solution of 28 mg of thiourea and 23 mg of sodium hydrogen-carbonate in 0.5 ml of water, and the mixture stirred at room temperature for 2 hours, poured into chloroform, washed with water, dried and evaporated under reduced pressure to yield 42 mg of diphenylmethyl 7β-(2-aminothiazol-4-yl)acetamido-7α-methoxy-3-(1-methyl-5-hydroxy-6-oxo-1,6-dihydro-1,3,4-triazin-2-yl)thiomethyl-1-dethia-1-oxa-3-cephem-4-carboxylate as powder in 39% yield.

Rf=0.30 (TLC plate precoated by silica gel/chloroform:methanol (10:1))

The following compounds may be prepared in a similar manner to that mentioned above.

| | A | E | M | COB |
|---|---|---|---|---|
| 2 | ⌬(thiazole: β-H₂N, N, S, CH₂CO—) | α—H | H | COOCHPh₂ |
| 3 | " | " | " | COOH |
| 4 | " | α—CH₃O | " | " |

PREPARATION 1

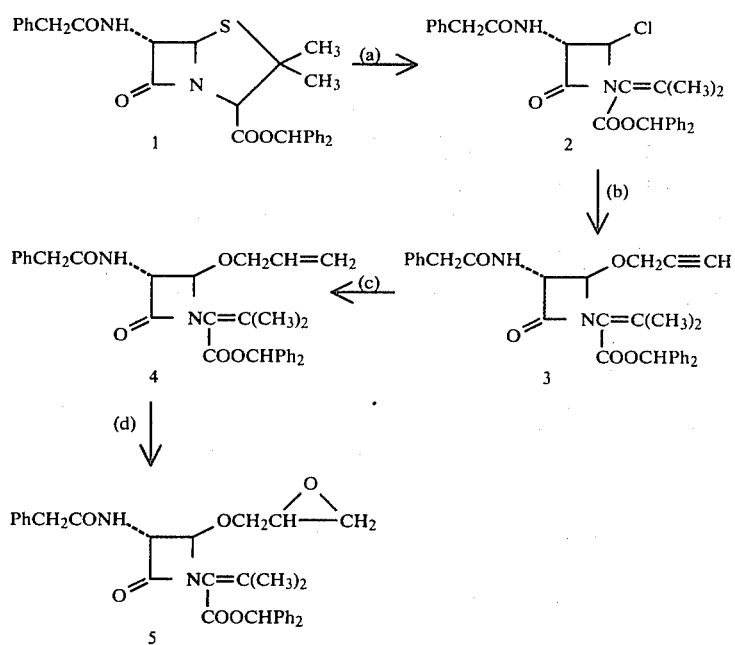

(a) To a suspension of 2.18 g of Compound 1 in 20 ml of chloroform is dropwise added a solution (9.5 ml; 17.5 mM) of chlorine in carbon tetrachloride at −20° C. to −30° C. with stirring. After about 30 minutes, the mixture gives a transparent yellow solution. This is washed with aqueous sodium hydrogen carbonate and saturated saline under ice cooling, dried over sodium sulfate, and evaporated to give Compound 2 (2.49 g) as yellow product.

NMR: $\delta^{CDCl_3}$ 1.97s3H, 2.25sH, 3.47s2H, 4.89dd(1;7 Hz)1H, 5.78d(1 Hz)1H, 6.55brd(7 Hz)1H, 6.83s1H, 7.2 ml 5H.

(b) To a solution of 537 mg of Compound 2 in 3 ml of propargyl alcohol is added 500 mg of silver tetrafluoroborate at −23° C. with stirring. After 1 hour, benzene and an aqueous sodium hydrogen carbonate are added thereto, and the mixture is stirred for a while and then filtered. The benzene layer is worked up in a conventional manner to yield Compound 3.

(c) A solution of 1.0 g of Compound 3 in 10 ml of methanol is catalytically hydrogenated in hydrogen atmosphere with 0.25 g of 5% palladium-calcium carbonate catalyst. The product is worked up in a conventional manner to yield 0.88 g of Compound 4 in 88% yield. m.p. 110°–112° C.

(d)-(1) Direct expoxidation.

To a solution of 0.88 g of Compound 4 in 9 ml of chloroform is added 0.54 g of m-chloroperbenzoic acid and allowed to stand at room temperature overnight. The reaction mixture is washed with an aqueous hydrogen sulfite solution, an aqueous sodium hydrogencarbonate solution, and then water, dried, and concentrated. The residue is chromatographed on 20 parts by volume of silica gel and eluted with a mixture of benzene and ethyl acetate (4:1) to yield 475 mg of Compound 5 in 51.7% yield.

(d)-(2) Via bromohydrin

To a solution of 148 mg of Compound 4 in 2.0 ml of dimethyl sulfoxide and 0.1 ml of water is added 60 mg of N-bromoacetamide under ice cooling, and the mixture is stirred at room temperature for 1.5 hours and then ice cooled. To this mixture is added 80 mg of potassium t-butoxide, and the mixture is stirred at the same temperature for 20 minutes, mixed with water, and extracted with ethyl acetate. The extract is worked up in a conventional manner to yield 120 mg of Compound 5.

IR: $\nu_{max}^{CHCl_3}$ 3410, 1775, 1720, 1680 cm$^{-1}$ m.p. 114°–115° C.

PREPARATION 2

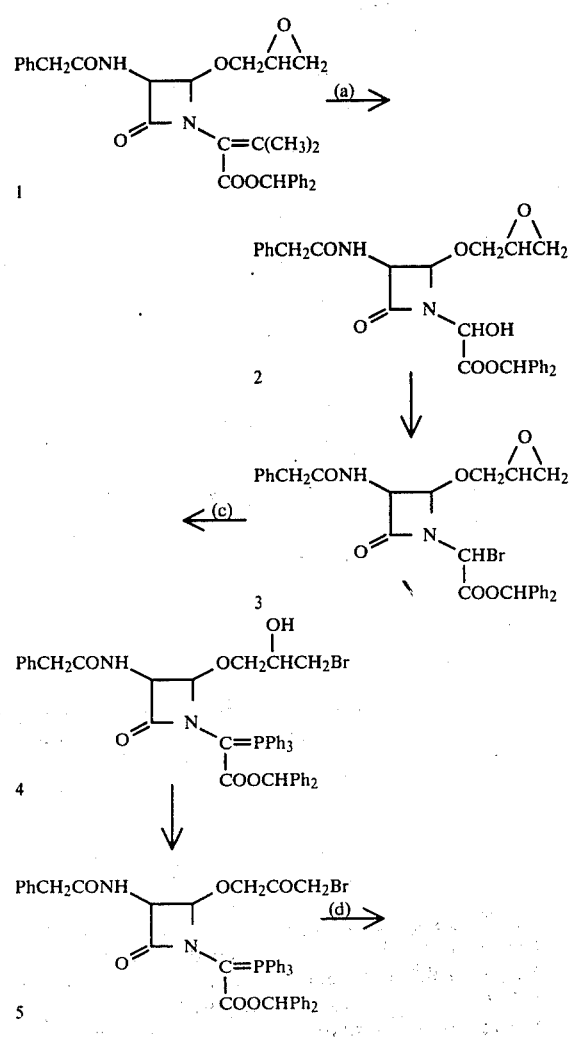

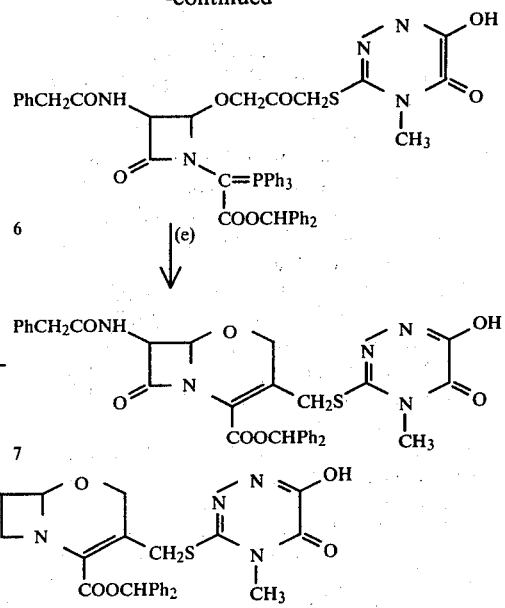

(a) To a solution of 7.31 g of Compound 1 in 100 ml of methylene chloride is introduced ozone for 20 minutes, and the resultant solution is stirred with 7.5 g of zinc powder and 100 ml of acetic acid at −78° to 0° C. for 30 minutes. The solid is filtered off, and the filtrate diluted with methylene chloride, washed with water, dried and evaporated to yield Compound 2 as foam in quantitative yield.

Rf=0.26, 0.17 (TLC plate precoated by silica gel/-benzene:ethyl acetate (1:1))

IR: $\nu_{max}^{CHCl_3}$ 1790, 1755, 1680 cm$^{-1}$

NMR: $\delta^{CDCl_3}$ 3.56.

The isomer at α position is isolated by chromatography on a column of silica gel.

(i) Rf=0.26 (TLC plate precoated by silica gel/benzene:ethyl acetate (1:1))

IR: $\nu_{max}^{CHCl_3}$ 1785, 1750, 1675 cm$^{-1}$

NMR: $\delta^{CDCl_3}$ 3.57s2H, 3.63s2H, 4.85d(4 Hz)1H, 5.30dd(4; 9 Hz)1H, 5.66s1H, 7.00s.

(ii)Rf=0.17 (TLC plate precoated by silica gel/benzene:ethyl acetate (1:1))

IR: $\nu_{max}^{CHCl_3}$ 1790, 1750, 1680 cm$^{-1}$

NMR: $\delta^{CDCl_3}$ 3.58s4H, 5.53s1H, 6.97s. [the isomer]

(b) To a solution of 5.07 g of Compound 2 in 80 ml of methanol are added 1.82 ml of N-methylmorpholine and 1.28 ml of thionyl bromide, and the mixture stirred for 20 minutes and poured into a mixture of ice water and ethyl acetate. The ethyl acetate layer is separated, washed with water, dried and evaporated under reduced pressure. The residue (7.49 g) is dissolved in 80 ml of methylene chloride and mixed with 3.19 g of triphenylphosphine, and the mixture stirred at room temperature for 40 minutes and poured into a mixture of ethyl acetate and ice water containing 5% sodium hydrogencarbonate. The ethyl acetate layer is separated, washed with water, dried and evaporated under reduced pressure. The residue (10.12 g) is chromatographed on 140 g of silica gel and eluted with benzene-ethyl acetate (1:1) to yield 7.06 g of Compound 4 as foam in 71.5% yield.

Rf=0.46 (benzene:ethyl acetate (1:2)); 0.20 (TLC plate precoated by silica gel/benzene:ethyl acetate (1:1))

IR: $\nu_{max}^{CHCl_3}$ 1770, 1665, 1630 cm$^{-1}$ (c) To a solution of 8.79 g of Compound 4 in 200 ml of acetone is added Jones Reagent (2.5 mole/L), and the mixture stirred for 1 hour, mixed with a small amount of isopropanol, stirred for 15 minutes and filtered. The filtrate is mixed with ethyl acetate, washed with 5% aqueous sodium hydrogencarbonate and water, dried and evaporated under reduced pressure to yield 8.40 g of Compound 5 as foam in 95.8% yield.

Rf=0.64 (TLC plate precoated by silica gel/benzene:ethyl acetate (1:2))

(d) To a solution of 8.30 g of Compound 5 in 120 ml of dimethylformamide is added a solution of sodium 1-methyl-5-hydroxy-6-oxo-1,2-dihydro-1,3,4-triazin-2-ylmercaptide in dimethylformamide, prepared from a suspension of 1.56 g of the corresponding free mercaptan in methanol on addition of 49.4 ml of a solution (0.2 mole) of sodium methylate in methanol, and the mixture stirred for 40 minutes under ice-cooling, diluted with ethyl acetate, washed with water, 5% aqueous sodium hydrogencarbonate solution and then water successively, dried and evaporated under reduced pressure to yield 8.58 g of Compound 6 as foam in 89.5% yield.

Rf=0.30 (TLC plate precoated by silica gel/ethyl acetate)

IR: $\nu_{max}^{CHCl_3}$ 1775, 1710, 1690, 1670, 1620, 1595 cm$^{-1}$ (e) A solution of 66.5 g of Compound 6 in 100 ml of dioxane is refluxed overnight under heating at 120° C. in an oil bath and evaporated under reduced pressure. The residue is chromatographed on 150 g of silica gel and eluted with chloroform-methanol (200:1 to 50:1) to yield 3.0 g of Compound 7 as foam in 66.2% yield.

Rf=0.35 (ethyl acetate); 0.17 (TLC plate precoated by silica gel/chloroform:methanol (95:5))

(f) To a solution of 3.23 g of Compound 7 in 30 ml of methylene chloride are added 2.55 ml of N,N-dimethylaniline and 1.51 ml of trimethylchlorosilane, and the mixture stirred at room temperature for 1 hour, and mixed with 1.32 g of phosphorus pentachloride at −40° C. The mixture is stirred for 1.5 hours, mixed with 12 ml of methanol at −60° C., and then stirred at −60° C. for 5 minutes and at 0° C. for 30 minutes. The reaction mixture is treated in a conventional manner to yield 2.38 g of Compound 8 as colorless foam in 90.5% yield.

Rf=0.08 (TLC plate precoated by silica gel/ethyl acetate)

IR: $\nu_{max}^{CHCl_3}$ 1795, 1715, 1690 (shoulder), 1585 cm$^{-1}$

NMR: $\delta^{CDCl_3+CD_3OD}$ 3.31s3H, 4.04brs2H, 4.52brs2H, 4.97d(4 Hz)1H.

PREPARATION 3

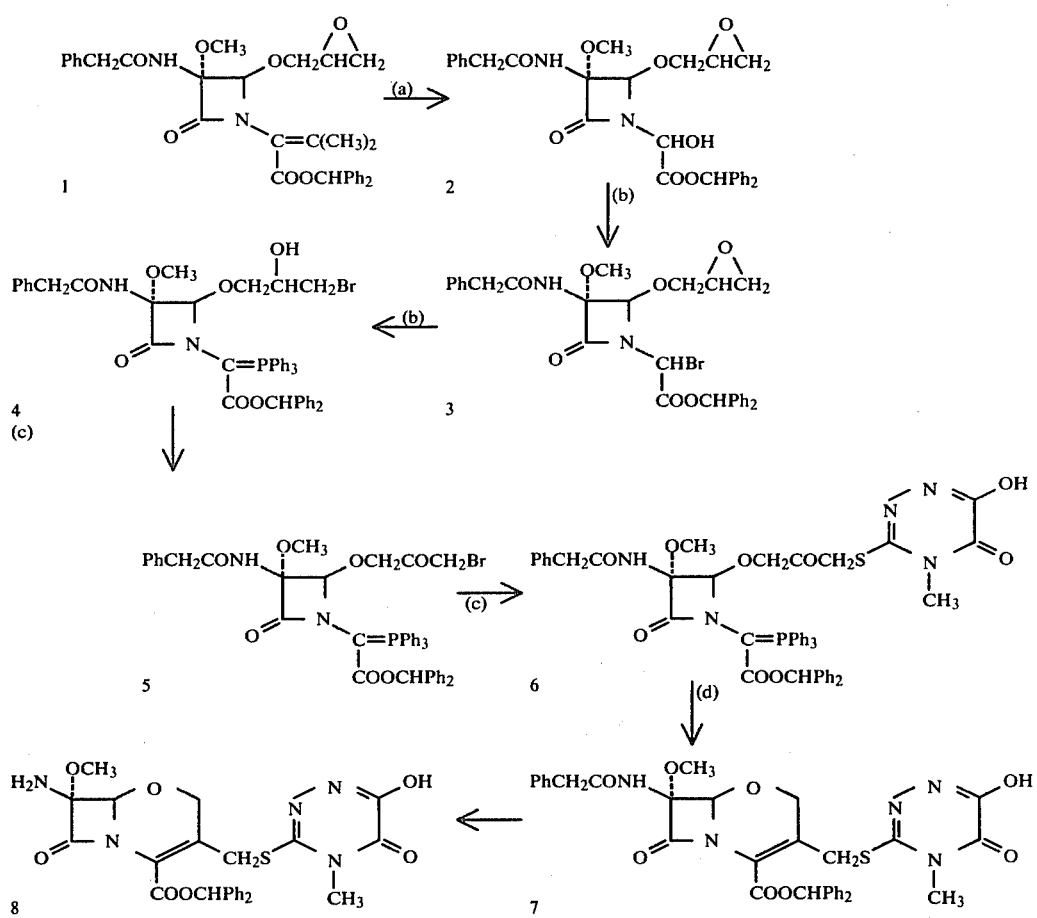

(a) To a solution of 11.1 g of Compound 1 in 160 ml of methylene chloride is introduced ozone at −78° C., and the resultant solution is stirred with 160 ml of acetic acid, 11.1 g of activated zinc powder and methylene chloride, until the temperature of the reaction mixture rises to 0° C., and filtered. The filtrate is washed with water, dried and evaporated under reduced pressure to yield 10.22 g of Compound 2 as colorless foam in 96.1% yield.

IR: $\nu_{max}^{CHCl_3}$ 1775, 1750, 1685, 1495 cm$^{-1}$ (b) To a solution of 10.10 g of Compound 2 in 150 ml of methylene chloride are dropwise added 2.81 g of N-methylmorpholine and 2.15 ml of thionyl bromide under ice-cooling, and the mixture stirred for 20 minutes and poured into a mixture of ice water and ethyl acetate. The organic layer is separated, washed with aqueous sodium chloride solution containing hydrogen bromide, dried and evaporated under reduced pressure. The residue is dissolved in 150 ml of methylene chloride and mixed with 5.35 g of triphenyl phosphine, and the mixture stirred at room temperature for 1 hour. The reaction mixture is washed with 5% aqueous sodium hydrogen-carbonate solution and aqueous sodium chloride solution, dried over magnesium sulfate and evaporated under reduced pressure. The residue is chromatographed on 30 parts by volume of silica gel and eluted with benzene-ethyl acetate (1:1) to yield 9.92 g of Compound 4 in 61.5% yield.

(c) To a solution of 7.30 g of Compound 4 in 280 ml of acetone is added 1.15 equivalents of Jones Reagent, and the mixture stirred for 50 minutes, mixed with isopropanol, stirred for 15 minutes and filtered. The filtrate is diluted with 400 ml of ethyl acetate, washed with 5% aqueous sodium hydrogencarbonate solution and aqueous sodium chloride solution dried over magnesium sulfate and evaporated to yield Compound 5, which is dissolved in 110 ml of dimethylformamide. To the solution is dropwise added a solution of 1 molar equivalent of sodium 1-methyl-5-hydroxy-6-oxo-1,2-dihydro-1,3,4-triazin-2-ylmercaptide in dimethylformamide under ice-cooling. The reaction mixture is stirred at 0° C. for 1 hour and poured into a mixture of ice water and ethyl acetate. The organic layer is separated, washed with water, dried and evaporated under reduced pressure to yield 7.65 g of Compound 6.

(d) A solution of 10.35 g of Compound 6 in 200 ml of dioxane is refluxed under heating for 6 hours and evaporated under reduced pressure. The residue is chromatographed on 250 g of silica gel to yield 3.85 g of Compound 7 in 52.7% yield.

IR: $\nu_{max}^{CHCl_3}$ 1783, 1710, 1690, 1590 cm$^{-1}$

NMR: $\delta^{CDCl_3}$ 3.35s3H, 3.50s3H, 3.70s2H, 4.05s2H, 4.53s2H, 5.13s1H, 6.77s1H, 7.00s1H, 7.2–7.6 m, 11.03s1H.

Rf=0.34 (TLC plate precoated by silica gel/ethyl acetate)

(e) Compound 7 (1.34 g) is stirred in the presence of 1.52 ml of dimethylaniline and 0.60 ml of dimethylsilyl dichloride in methylene chloride for 60 minutes to yield the corresponding silyl compound, the latter is treated with 1.04 g of phosphorus pentachloride at −25° C. to yield the corresponding iminochloride compound, and the latter stirred in 20 ml of methanol at 0° C. for 40 minutes and mixed with 2.6 ml of diethylamine. The mixture is stirred for 30 minutes, diluted with ethyl acetate, washed with water, dried and evaporated under reduced pressure. The residue is washed with petroleum ether and then ether to yield 0.98 g of Compound 8 as powder in 89% yield.

IR: $\nu_{max}^{CHCl_3}$ 1790, 1720, 1710, 1690, 1595 cm$^{-1}$

NMR: $\delta^{CDCl_3}$ 2.15brs2H, 3.32s3H, 3.50s3H, 4.03s2H, 4.53s2H, 4.87s1H, 6.95s1H, 7.1–7.6 m Rf=0.21 (TLC plate precoated by silica gel/ethyl acetate)

PHYSICAL DATA FOR EXAMPLES

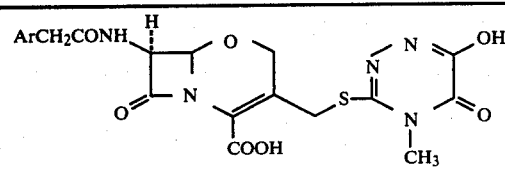

| Ar | mp | IR:$\nu_{max}^{KBr}$ (cm$^{-1}$) | Rf value (TLC) (CH$_3$COOC$_2$H$_5$:CH$_3$COOH:H$_2$O) |
|---|---|---|---|
| Ph– | powder | 1782, 1710, 1680, 1585. | 0.28 (8:1:1) |
| NH$_2$–(thiazole)– (CF$_3$COOH) | " | 1785, 1707, 1680, 1588. | 0.64 (3:1:1) |

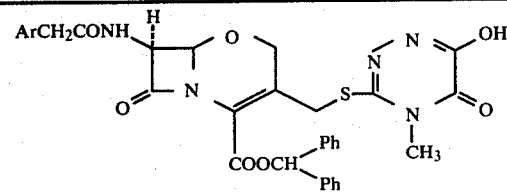

| Ar | mp | IR:$\nu_{max}^{CHCl_3}$ (cm$^{-1}$) | NMR: δ (ppm) | Rf value (TLC) (CH$_3$COOC$_2$H$_5$) |
|---|---|---|---|---|
| Ph– | foam | 1800, 1720, 1690, 1590. | 3.31s3H, 3.65s2H, 4.06bs2H, 4.46bs2H, 5.02d(4Hz)1H, 5.75dd(4;9Hz)1H, 7.00s15H. (CDCl$_3$) | 0.35 |
| NH$_2$–(thiazole)– | powder | | 3.23s3H, 3.40s2H, 4.07bs2H, 4.65bs2H, 5.23d(4Hz)1H, 5.67dd(4;9Hz)1H, 6.30s1H, 6.88s1H, 6.97s1H, 7.27–7.77m10H. (d$_6$DMSO) | |

-continued

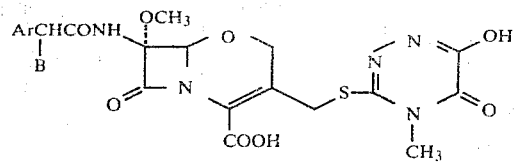

| Ar | B | mp | IR: $\nu_{max}^{KBr}$ (cm$^{-1}$) | Rf value (TLC) (CH$_3$COOC$_2$H$_5$:CH$_3$COOH:H$_2$O) |
|---|---|---|---|---|
| phenyl | H | powder | 1785, 1710, 1680, 1588. | 0.24 (8:1:1) |
| 2-amino-thiazol-4-yl (CF$_3$COOH) | " | " | 1781, 1705, 1680, 1585. | 0.50 (3:1:1) |
| thien-3-yl | —COOH | " | 1783, 1710, 1586. | 0.63 (3:1:1) |
| 3-hydroxyphenyl | " | " | 1782, 1710, 1587. | 0.62 (3:1:1) |
| 4-hydroxyphenyl | " | " | 1780, 1708, 1587, 1515. | 0.10 (5:1:1) |
| 4-(NH$_2$COO)phenyl | " | " | 1780, 1710, 1588, 1510. | 0.14 (5:1:1) |
| 3-fluoro-4-hydroxyphenyl | " | " | 3260, 1780, 1710, 1630, 1590, 1515. | 0.22 (5:1:1) |

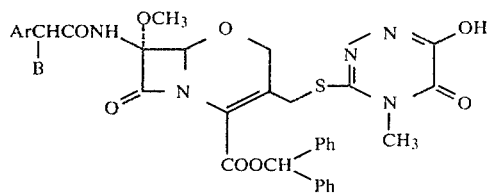

| Ar | B | mp | IR: $\nu_{max}^{CHCl_3}$ (cm$^{-1}$) | NMR: δ (ppm) | Rf value (TLC) (solvent) |
|---|---|---|---|---|---|
| phenyl | H | foam | 1783, 1710, 1690, 1590. | 3.35s3H, 3.50s3H, 3.70s2H, 4.05s2H, 4.53s2H, 5.13s1H, 6.77s1H, 7.00s1H, 2.2-7.6m15H, 11.03s1H. (CDCl$_3$) | 0.34 (CH$_3$COOC$_2$H$_5$) |
| 2-amino-thiazol-4-yl | " | powder | | 3.25s3H, 3.52bs(3+2)H, 4.05bs2H, 4.85bs2H, 5.07s1H, 6.27s1H, 6.97s1H, 7.2-7.6m10H. (CDCl$_3$) | 0.30 (CHCl$_3$: CH$_3$OH =10:1) |
| thien-3-yl | —COOCHPh$_2$ | foam | 1785, 1720, 1715, 1695, 1590. | 3.30s3H, 3.43s3H, 4.02bs2H, 4.42bs 2H, 5.00s1H, (5.08+5.12)s1H, 6.97s 1H, 7.00s1H, 7.1-7.9m23H, 10.85bs1H. (CDCl$_3$) | 0.47 (CH$_3$COOC$_2$H$_5$) |
| CH$_3$O-phenyl-CH(O-phenyl)- | —COOCH$_2$-(4-OCH$_3$)phenyl | " | 1785, 1720, 1712, 1690, 1590. | 3.30s3H, 3.48s3H, 3.75s3H, 3.80s3H, 4.00bs2H, 4.45bs2H, 4.70s1H, 4.93s 2H, 5.10s1H, 5.17s2H, 7.00s1H, 6.8-7.6m22H, 10.80bs1H. | 0.47 (CH$_3$COOC$_2$H$_5$) |
| 4-hydroxyphenyl | —COOCHPh$_2$ | " | — | 3.30s3H, (3.43+3.47)s3H, 4.07bs2H, 4.40bs2H, 4.73s1H, (5.07+5.10)s1H, 7.00s1H, 6.7-7.6m24H. (CDCl$_3$+CD$_3$OD) | 0.50 (CH$_3$COOC$_2$H$_5$) |
| 4-(NH$_2$COO)phenyl | " | " | — | 3.28s3H, (3.47+3.50)s3H, 4.00bs2H, 4.30bs2H, (4.78+4.81)s1H, 5.03s1H, 6.90s1H, 6.97s1H, 7.0-7.6m24H. (CDCl$_3$+CD$_3$OD) | 0.24 (CHCl$_3$: CH$_3$OH =9:1) |

-continued

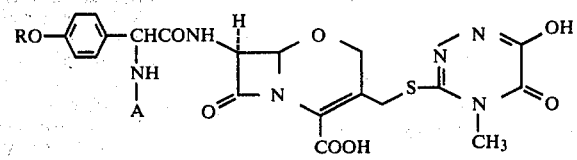

| R | A | mp | IR: $\nu_{max}^{KBr}$ (cm$^{-1}$) | NMR: $\delta^{CD_3OD}$ (ppm) | Rf value (TLC) solvent system (CH$_3$COOC$_2$H$_5$: CH$_3$COOH:H$_2$O) |
|---|---|---|---|---|---|
| H | −CON⟨(C=O)(C=O)⟩N−C$_2$H$_5$ (Na Salt) | powder | 1783, 1710, 1680, 1588, 1514. | | 0.40 (5:1:1) |
| NH$_2$CO | " | " | 3445, 1785, 1710, 1680 1590. | 1.21t(7Hz)3H, 3.43s3H, 3.67m4H, 4.07q(7Hz)2H, 4.20s2H, 4.53bs2H, 5.08d(4Hz)1H, 5.60m(1+1)H, (7.13+7.53)ABq(8Hz)4H. (CD$_3$OD) | 0.37 (5:1:1) |
| H | −CON⟨(C=O)⟩N−SO$_2$CH$_3$ | " | 1781, 1735, 1705, 1671, 1592. | | 0.30 (5:1:1) |
| " | −CO−N(CH$_3$)−CONHCH$_3$ | " | 1788, 1707, 1676, 1590. | 2.79s3H, 3.19s3H, 3.47s3H, 4.20bs2H, 4.58bs2H, 5.41s1H, (6.75+7.34)ABq(8Hz)4H. (CD$_3$OD) | 0.52 (5:1:1) |
| " | H (CF$_3$COOH) | " | 1783, 1705, 1680, 1590. | | 0.40 (3:1:1) |

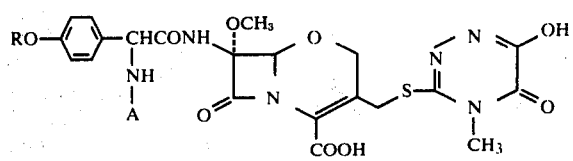

| H | −CON⟨(C=O)(C=O)⟩N−C$_2$H$_5$ | " | 1773, 1707, 1680, 1590, 1515. | 1.17t(7Hz)3H, 3.04bs3H, 3.50bs3H, 5.08s1H, 5.43s1H, (6.80+7.40)ABq(9Hz)4H (D$_2$O) | 0.33 (5:1:1) |
| NH$_2$CO | " | " | 1782, 1709, 1675, 1588. | 1.21t(7Hz)3H, 3.43s3H, 3.53s3H, 4.10bs2H, 5.01s1H, 5.52s1H, (7.06+7.49)ABq(8Hz)4H (CDCl$_3$+CD$_3$OD) | 0.33 (5:1:1) |
| H | −CON⟨(C=O)⟩N−SO$_2$CH$_3$ | " | 1772, 1707, 1680, 1590, 1515 | — | 0.39 (5:1:1) |
| H | −CO−N(CH$_3$)−CONHCH$_3$ | " | 3360, 1780, 1710, 1680, 1590. | 2.80s3H, 3.23s3H, 3.50s3H, 3.53s3H, 4.17bs2H, 4.43bs2H, 5.08s1H, 5.43s1H, (6.83+7.40) ABq(8Hz)4H. (CDCl$_3$+CD$_3$OD) | 0.19 (5:1:1) |
| H | H (CF$_3$COOH) | " | 1782, 1707, 1675, 1590, | 3.47bs6H, 4.17bs2H, 4.48bs2H, 5.08bs1H, (6.87+7.47)ABq(8Hz)4H (CD$_3$OD) | 0.15 (5:1:1) |
| NH$_2$CO | H (CF$_3$COOH) | " | 1780, 1700, 1675, 1588. | 3.43s3H, 355s3H, 4.15bs2H, 4.47bs2H, 5.11s1H, 5.17s1H, (7.20+7.61)ABq(8Hz)4H. (CD$_3$OD) | 0.34 (3:1:1) |

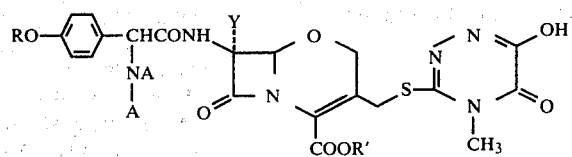

| Y | R | R' | A | mp | IR: $\nu_{max}$ (cm$^{-1}$) | NMR: $\delta$ (ppm) | Rf value (TLC) solvent system (CHCl$_3$: CH$_3$OH) |
|---|---|---|---|---|---|---|---|

-continued

| | | | | NMR | |
|---|---|---|---|---|---|
| H | H | -CH2-⌬-NO2 | -CON⟨N-C2H5⟩ (piperazine with CON) | | 1.20t(7Hz)3H, 3.40s3H, 3.60bs2H, 3.90bs2H, 4.13bs2H, 4.53bs2H, 5.02d(4Hz)1H, 5.33s1H, 5.43s2H, 5.58d(4Hz)1H, (6.75+7.27ABq(8Hz)4H, (7.62+8.22)ABq(9Hz)4H. (CDCl3+CD3OD) | 0.19 (9:1) |
| " | " | -CH⟨Ph,Ph⟩ | -C(=O)-O-C(CH3)3 | foam | 1.43s9H, 3.37s3H, 4.10bs2H, 4.48bs2H, 5.03d(4Hz)1H, 5.18bs1H, 5.67d(4Hz)1H, 6.80ABq(8Hz)2H, 6.98s1H, 7.2-7.6m12H. | |
| —OCH3 | " | " | " | " | 1790, 1710, 1690, 1595, 1495. | 1.40s9H, 3.35s3H, 3.55s3H, 4.03bs2H, 4.33b2H, 5.07s1H, 3.12bs1H, 6.77ABq(8Hz)2H, 6.95s1H, 7.2-7.6m12H. (CDCl3+CD3OD) | |
| " | NH2CO— | " | " | " | 1780, 1735, 1385. | 1.55s9H, 3.24s3H, 3.54s3H, 3.96bs2H, 4.28bs2H, 5.01s1H, 6.91s1H, 6.95ABq(8Hz)2H. | 0.15 (9:1) |

We claim:

1. A compound of the formula

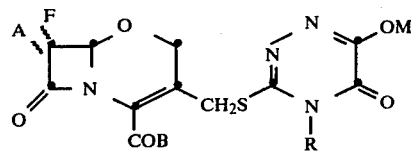

wherein R is lower alkyl; E is hydrogen or methoxy; M is hydrogen or a hydroxy protecting group; COB is carboxy, protected carboxy or a carboxy salt; and A is
(1) azido, isocyanato, isocyano;
(2) amino;
(3) trimethylsilylamino, methoxydimethylsilylamino, dimethoxymethylsilylamino or trimethylstannylamino;
(4) a hydrocarbonated amino group selected from the group consisting of 1-carbethoxy-1-propen-2-ylamino, 1-carbamoyl-1-propen-2-ylamino, 1-N-phenylcarbamoyl-1-buten-2-ylamino, 1-propen-2-ylamino, 1-phenylpentene-2-ylamino, methylamino, t-butylaminotritylamino, methylideneamino, ethylideneamino, 1-halo-2-phenylethylideneamino, 1-chlorobenzylideneamino, 1-methoxybenzylideneamino, 1-loweralkoxy-2-phenylethylideneamino, 1-loweralkoxy-2-phenoxyethylideneamino and di-t-butyl-4-hydroxybenzylideneamino;
(5) a diacylamino derived from a $C_4$ to $C_{10}$ polybasic carboxylic acid;
(6) a o-nitrophenylsulfenylamino group; or
(7) an acylamino group wherein the acyl group is
 (a) $C_1$-$C_{10}$ alkanoyl or benzoyl;
 (b) halo-$C_1$-$C_4$ alkanoyl;
 (c) trifluoromethylthioacetyl or cyanoacetyl;
 (d) (2- or 4-pyridon-1-yl)acetyl or (2-iminothiazolin-4-yl)acetyl;
 (e) a group of the formula Ar—CQQ'—CO— wherein Q and Q' are hydrogen or methyl; Ar is a cyclic group selected from phenyl, dihydrophenyl, furyl, thienyl, pyrrolyl, oxazolyl, isoxazolyl, oxadiazolyl, oxatriazolyl, thiazolyl, isothiazolyl, thiadiazolyl, thiatriazolyl, pyrazolyl, imidazolyl, triazolyl, tetrazolyl, pyridyl, pyrimidyl, pyridinyl, pyridazinyl or triazinyl which cyclic groups are unsubstituted or are substituted by halogen, lower alkyl, hydroxy, both a halogen and a hydroxy, lower alkoxy, formyloxy, acetyloxy, propionyloxy, pentanoyloxy, carbamoyloxy, benzoyloxy, methoxycarbonyloxy, ethoxycarbonyloxy, t-butoxycarbonyloxy, benzyloxycarbonyloxy, nitrobenzyloxycarbonyloxy, methoxybenzyloxycarbonyloxy, benzyloxy, methoxybenzyloxy, aminobenzyloxy, methylbenzyloxy, isopropylbenzyloxy, nitrobenzyloxy, diphenylmethoxy, phthalidyloxy, phenoxy, tolyloxy, xylyloxy, indanyloxy, amino, $C_1$-$C_{10}$ alkanoylamino, lower alkanesulfonylamino, hydroxymethyl, or aminomethyl;
 (f) a group of the formula Ar—G—CQQ'—CO— wherein Ar, Q and Q' are the same as defined above and G is oxygen or sulfur;
 (g) a group of the formula Ar—CHT—CO— wherein Ar is the same as defined above; T is (i) hydroxy, formyloxy, acetyloxy, propionyloxy, pentanoyloxy, carbamoyloxy, benzoyloxy, methoxycarbonyloxy, ethoxycarbonyloxy, t-butoxycarbonyloxy, benzyloxycarbonyloxy, nitrobenzyloxycarbonyloxy or methoxybenzyloxycarbonyloxy; (ii) carboxy, carboxy protected by lower alkoxy, benzyloxy, methoxybenzyloxy, aminobenzyloxy, methylbenzyloxy, isopropylbenzyloxy, nitrobenzyloxy, diphenylmethoxy, phthalidyloxy, phenoxy, tolyloxy, xylyloxy, indanyloxy, cyano or carbamoyl; or (iii) sulfo or lower alkoxysulfonyl;
 (h) a group of the formula

L—O—CO— wherein L is t-butyl, 1,1-dimethylpropyl, cyclopropylmethyl, 1-methylcyclohexyl, isobornyl, ethoxy-t-butyl, 2-alkanesulfonylethyl, 2,2,2-trichloroethyl, benzyl, methoxybenzyl, nitrobenzyl, aminobenzyl, diphenylmethyl, tolylmethyl, phenyl, xylyl or pyridylmethyl;

(i) a group of the formula $$Ar-\underset{NHW}{CH}-CO-$$

wherein Ar is the same as defined above; W is $C_1-C_{10}$ alkanoyl, halo-$C_1-C_4$ alkanoyl, or a group represented by the formula Ar—CQ-Q'—CO— as defined above, Ar—CO—, LOCO—, $$ArNHC-CH_2CO-, \quad R^1N\underset{NH}{\overset{CO}{\diagup\diagdown}}NCO-,$$

$$R^1SO_2N\underset{}{\overset{CO}{\diagup\diagdown}}NCO-,$$

$R^1NHCONR^2-CO-$, $R^1NHCSNR^2CO-$, $$R^1NHCNR^2CO-, \text{ or } R^1-N\underset{}{\overset{COCO}{\diagup\diagdown}}N-CO-,$$
$$\underset{NH}{\|} \qquad\qquad R^2$$

wherein Ar and L are as defined above and $R^1$ and $R^2$ are hydrogen, $C_1-C_4$ alkyl, or $C_1-C_{10}$ alkanoyl; or W is an enolic group of active carbonyl compounds represented by the formula $R^1CH_2\overset{|}{C}=CHCOOR^2$, $R^1CH_2\overset{|}{C}=CHCN$, $R^1CH_2\overset{|}{C}=CHCONHC_6H_5$,

[cyclic structures] =C—CH$_3$ or R$^1$CHC=CHCON wherein $R^1$ and $R^2$ are the same as defined above; or NHW is phthalimido or succinimido;

(j) an acyl group of the formula $$Ar-\underset{NOR^1}{\overset{\|}{C}}-CO-$$

wherein Ar and $R^1$ are the same as defined above; or (k) a 5-aminoadipoyl group in which the carboxy or amino group is optionally protected with a conventional carboxy or amino protecting group;

and when A is amino or an acyl group having an amino substituent, an acid addition salt of the compounds represented thereby; provided that when E is methoxy, E is in the 7-alpha position on the cephem ring.

2. A compound of claim 1 of the formula

[structure]

wherein R, E, M, COB and E are as defined in claim 1.

3. A compound of claim 2 wherein E is hydrogen.

4. A compound of claim 3 wherein A is an amino group.

5. A compound of claim 3 wherein A is a hydrocarbonated amino group.

6. A compound of claim 3 wherein A is azido, isocyanato, isocyano, trimethylsilylamino, methoxydimethylsilylamino, dimethoxymethylsilylamino or trimethylstannylamino.

7. A compound of claim 3 wherein A is an acylamino group.

8. A compound of claim 7 wherein R is methyl.

9. A compound of claim 8 wherein COB is protected carboxy.

10. A compound of claim 8 wherein COB is carboxy or a carboxy salt.

11. A compound of claim 8 wherein COB is carboxy or a pharmaceutically acceptable alkali metal or lower alkylamine salt.

12. A compound of claim 11 wherein M is hydrogen.

13. A compound of claim 12 wherein A is an acylamino group of the formula

Ar—CHT—CONH—

14. A compound of claim 13 wherein T is carboxy.

15. A compound of claim 12 wherein A is an acylamino group of the formula

Ar—CH$_2$—CONH—

16. A compound of claim 15 wherein Ar is phenyl or phenoxy.

17. A compound of claim 15 wherein Ar is 2-aminothiazol-4-yl- and its trifluoroacetic acid addition salt.

18. A compound of claim 12 wherein A is an acylamino group of the formula $$Ar-\underset{NHW}{CH}-CONH-$$

19. A compound of claim 18 wherein W is a group of the formula $$-CON\underset{}{\overset{O\quad O}{\diagup\diagdown}}N-CH_2-CH_3$$

20. A compound of claim 19 wherein Ar is phenyl, 4-hydroxyphenyl or 4-carbamoyloxyphenyl.

21. A compound of claim 18 wherein W is a group of the formula

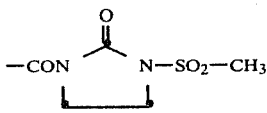

22. A compound of claim 21 wherein Ar is 4-hydroxyphenyl.

23. A compound of claim 18 wherein W is a group of the formula

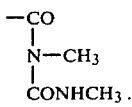

24. A compound of claim 23 wherein Ar is 4-hydroxyphenyl.

25. A compound of claim 12 wherein A is an acylamino group of the formula

26. A compound of claim 2 wherein E is methoxy.

27. A compound of claim 26 wherein A is an amino group.

28. A compound of claim 26 wherein A is trimethylsilylamino, methoxydimethylsilylamino, dimethoxymethylsilylamino or trimethylstannylamino.

29. A compound of claim 26 wherein A is an acylamino group.

30. A compound of claim 29 wherein R is methyl.

31. A compound of claim 30 wherein COB is protected carboxy.

32. A compound of claim 30 wherein COB is carboxy or a carboxy salt.

33. A compound of claim 30 wherein COB is carboxy or a pharmaceutically acceptable alkali metal or lower alkylamine salt.

34. A compound of claim 33 wherein M is hydrogen.

35. A compound of claim 34 wherein A is an acylamino group of the formula

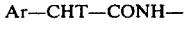

36. A compound of claim 35 wherein T is carboxy or protected carboxy.

37. A compound of claim 35 wherein T is carboxy.

38. A compound of claim 37 wherein Ar is 3-thienyl.

39. A compound of claim 37 wherein Ar is 3-hydroxyphenyl or 4-hydroxyphenyl.

40. A compound of claim 37 wherein Ar is phenyl substituted with a halogen and a hydroxy.

41. A compound of claim 40 wherein Ar is 2-fluoro-4-hydroxyphenyl or 2-fluoro-5-hydroxyphenyl.

42. A compound of claim 37 wherein Ar is 4-carbamoyloxyphenyl.

43. A compound of claim 34 wherein A is an acylamino group of the formula

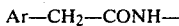

44. A compound of claim 43 wherein Ar is phenyl or phenoxy.

45. A compound of claim 43 wherein Ar is 2-aminothiazol-4-yl.

46. A compound of claim 34 wherein A is an acylamino group of the formula

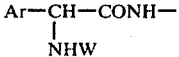

47. A compound of claim 46 wherein W is a group of the formula

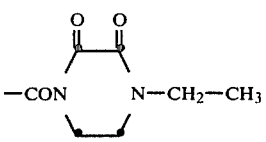

48. A compound of claim 47 wherein Ar is phenyl, 3-hydroxyphenyl or 4-hydroxyphenyl.

49. A compound of claim 47 wherein Ar is 4-carbamoyloxyphenyl.

50. A compound of claim 46 wherein W is a group of the formula

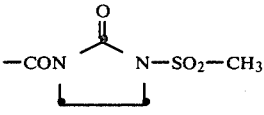

51. A compound of claim 49 wherein Ar is phenyl, 3-hydroxyphenyl or 4-hydroxyphenyl.

52. A compound of claim 50 wherein Ar is 4-hydroxyphenyl.

53. A compound of claim 46 wherein W is a group of the formula

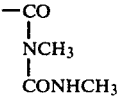

54. A compound of claim 52 wherein Ar is 4-hydroxyphenyl.

55. A compound of claim 53 wherein Ar is 4-hydroxyphenyl or 4-carbamoyloxyphenyl.

56. A compound of claim 1 of the formula

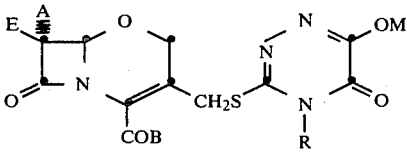

wherein A is benzoylamino, 1-chlorobenzylideneamino, or 1-methoxybenzylideneamino.

* * * * *